United States Patent [19]

Miyake et al.

[11] 4,430,445
[45] Feb. 7, 1984

[54] NOVEL BASIC IMIDAZOLYLMETHYLSTYRENE COMPOUND, ITS POLYMER, A PROCESS FOR THE PREPARATION THEREOF AND A USE AS ION EXCHANGE RESIN

[75] Inventors: Tetsuya Miyake, Suginami; Kunihiko Takeda; Keishi Tada, both of Yokohama, all of Japan

[73] Assignee: Asahi Kasei Kogyo Kabushiki Kaisha, Osaka, Japan

[21] Appl. No.: 335,943

[22] Filed: Dec. 30, 1981

Related U.S. Application Data

[63] Continuation-in-part of Ser. No. 165,451, Jul. 2, 1980, abandoned.

[30] Foreign Application Priority Data

Jul. 19, 1979 [JP] Japan .................................. 54-90901
Jan. 16, 1981 [JP] Japan .................................. 56-3739
Jan. 19, 1981 [JP] Japan .................................. 56-4954
Jan. 19, 1981 [JP] Japan .................................. 56-4955

[51] Int. Cl.$^3$ .................... B01J 39/20; C08F 26/06
[52] U.S. Cl. ............................ 521/38; 526/262; 548/335; 548/336; 548/337; 548/338
[58] Field of Search ............ 548/335, 336, 337, 338; 521/38; 526/310, 258, 262

[56] References Cited

U.S. PATENT DOCUMENTS

| | | | |
|---|---|---|---|
| 3,709,901 | 6/1973 | Drober et al. | 548/336 |
| 3,764,690 | 10/1973 | Drober et al. | 548/335 |
| 3,796,704 | 3/1974 | Metzger | 548/336 |
| 4,107,098 | 8/1978 | Tamura et al. | 521/25 |
| 4,115,578 | 9/1978 | Miller et al. | 548/337 |
| 4,226,878 | 10/1980 | Iizuka et al. | 548/335 |
| 4,284,641 | 8/1981 | Thorogood | 548/335 |

FOREIGN PATENT DOCUMENTS 2845406 3/1979 Fed. Rep. of Germany ...... 548/335

OTHER PUBLICATIONS

Textbook of Polymer Sci., Fred W. Billmeyer, Jr., from p. 263.
O. Wallach, "Ueber Oxaline und Glyoxaline. II.", Chemische Berichte, 16, 1365, (1877).
G. Wyss, "Zur Kenntniss des Glyoxalins.", Chemische Berichte, 10, 1365, (1877).
J. E. Jalamose et al., Polymer, 1973, vol. 14, pp. 639–644, Dec.

*Primary Examiner*—Joseph L. Schofer
*Assistant Examiner*—Peter F. Kulkosky
*Attorney, Agent, or Firm*—Sprung, Horn, Kramer & Woods

[57] ABSTRACT

Novel imidazolylmethylstyrene compounds which are basic compounds and have excellent resistance to oxidation and high polymerizability are disclosed. The basic compound of the present invention is prepared by reacting a halogenomethyl-styrene with an imidazole compound, and can be used, for example, as a curing agent for epoxy resins. The imidazolymethylstyrene compounds are readily homopolymerized or copolymerized to provide linear homopolymers, linear copolymers or cross-linked copolymers having pendant imidazolylmethylphenyl groups. These polymers have greater resistance to oxidation than the homologues, and are useful as an ion exchange resin, extractant of metals, sizing agent and antistatic agent.

46 Claims, No Drawings

NOVEL BASIC IMIDAZOLYLMETHYLSTYRENE COMPOUND, ITS POLYMER, A PROCESS FOR THE PREPARATION THEREOF AND A USE AS ION EXCHANGE RESIN

This application is a continuation-in-part of application Ser. No. 165,451, filed July 2, 1980, now abandoned.

This invention relates to a novel basic compound, its polymer, a process for the preparation thereof and a use as an ion exchange resin. More particularly, this invention is concerned with a basic compound having an imidazole ring and capable of being homopolymerized and copolymerized, a process for the preparation thereof, a linear homopolymer, linear copolymer and cross-linked copolymer having pendant imidazolylmethylphenyl groups, a process for the preparation thereof and the use of the cross-linked copolymer as an ion exchange resin.

To now, many imidazole ring-containing compounds are known, including, for example, 1-methylimidazole, 1-benzylimidazole, 2-phenylimidazole, 4(5)-methylimidazole and 4,5-dinitroimidazole. Any of these imidazoles, however, lacks polymerizability, so that its utility is low. For example, such imidazoles cannot be polymerized according to customary procedures to give a polymer which can be used as an ion exchange resin. A special polymerization technique of performing "oxidative coupling" after incorporation of hydroxyl groups may be effected for such imidazoles, but it is still disadvantageously inapplicable to copolymerization.

Also known are imidazoles having a vinyl group, such as N-vinylimidazole and 4-[p-(1-imidazolylmethyl)phenyl]-1-butene. N-vinylimidazole is basic due to the inherent nature of the imidazole ring and is capable of being polymerized due to the presence of the vinyl group. Hence, its utility should be high, but the compound has a drawback that it is susceptible to oxidation. Further, 4-[p-(1-imidazolylmethyl)phenyl]-1-butene may be ionically polymerized by special means, but it can hardly be regarded as having a polymerizable double bond from the viewpoint of polymer chemistry. For example, the compound cannot be polymerized by polymerization methods which are customary and important in the polymer industry, such as radical polymerization.

We have made researches on reactions between halogenomethylstyrenes and imidazole compounds with a view to developing an imidazole ring containing styrene which can be easily polymerized, and, as a result, we have succeeded in synthesizing novel basic styrene compounds, more particularly imidazolylmethylstyrene compounds, which are basic due to the inherent nature of the imidazole ring, can be readily quaternized by a quaternizing agent such as chloromethane and can be radical polymerized. We have further studied the polymerizability of the imidazolylmethylstyrene compounds, and have found that they can be copolymerized at an optional molar ratio with a typical monomer, such as styrene or methyl methacrylate. For instance, the monomer reactivity ratio ($r_1$) of imidazolylmethylstyrene to styrene was 1.1 and that ($r_2$) of styrene to imidazolylmethylstyrene was 0.95. We have attempted various homopolymerization and copolymerization reactions, whereby we have obtained various practically useful homopolymers and copolymers. Based on these findings, we have completed this invention.

It is, therefore, an object of the present invention to provide a novel class of imidazolylmethylstyrene compounds which have excellent resistance to oxidation and high polymerizability.

It is another object of the present invention to provide a process for the preparation of such a novel class of imidazolylmethylstyrene compounds.

It is a further object of the present invention to provide a linear homopolymer, linear copolymer and cross-linked copolymer having pendant imidazolylmethylphenyl groups which can be advantageously used as an ion exchange resin and for other purposes.

It is still a further object of the present invention to provide a process for the preparation of such a linear homopolymer, linear copolymer and cross-linked copolymer.

It is an additional object of the present invention to provide a method of ion exchange using the above-mentioned cross-linked copolymer as an ion exchange resin.

The foregoing and other objects, features and advantages of the present invention will be apparent to those skilled in the art from the following detailed description and appended claims.

In accordance with one aspect of the present invention, there is provided a basic compound represented by the following structural formula (I):

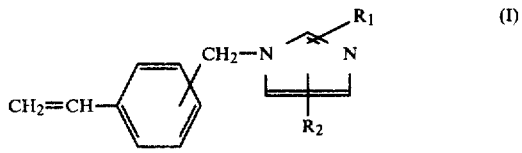

wherein $R_1$ and $R_2$ each independently stand for a hydrogen atom, a straight chain or branched alkyl group having 1 to 17 carbon atoms, a phenyl group unsubstituted or substituted with one or more substituents selected from $C_1-C_8$ straight chain or branched alkyl groups, halogen atoms and an amino group, a naphthyl group, an aralkyl group having as an alkyl moiety a $C_1-C_4$ straight chain or branched alkylene group and as an aryl moiety a phenyl group unsubstituted or substituted with one or more substituents selected from halogen atoms and an amino group, a pyridyl group unsubstituted or substituted with one or more substituents selected from $C_1-C_4$ straight chain or branched alkyl groups, halogen atoms and an amino group, or a nitro group.

As preferred examples of $R_1$ and $R_2$, there can be mentioned a hydrogen atom, a methyl group, an ethyl group, a normal propyl group, an isopropyl group, a phenyl group, a benzyl group, a pyridyl group and a nitro group. $R_1$ and $R_2$ may be the same or different.

The position of the imidazol-1-ylmethyl group relative to the vinyl group in the compound of the formula (I) may be the ortho-, meta- or para-position, and is preferably the meta- or para-position. It is preferred that $R_1$ be located at the 2-position of the imidazole ring.

In accordance with the second aspect of the present invention, there is provided a process for the preparation of a basic compound represented by the following structural formula (I):

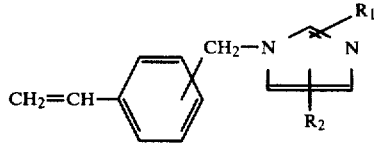

$$\text{(I)}$$

wherein $R_1$ and $R_2$ each independently stand for a hydrogen atom, a straight chain or branched alkyl group having 1 to 17 carbon atoms, a phenyl group unsubstituted or substituted with one or more subsubstituents selected from $C_1$-$C_8$ straight chain or branched alkyl groups, halogen atoms and an amino group, a naphthyl group, an aralkyl group having as an alkyl moiety a $C_1$-$C_4$ straight chain or branched alkylene group and as an aryl moiety a phenyl group unsubstituted or substituted with one or more substituents selected from halogen atoms and an amino group, a pyridyl group unsubstituted or substituted with one or more substituents selected from $C_1$-$C_4$ straight chain or branched alkyl groups, halogen atoms and an amino group, or a nitro group;

which comprises reacting a halogenomethylstyrene represented by the following structural formula (II):

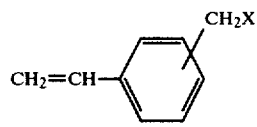

$$\text{(II)}$$

wherein X stands for Cl, Br or I, with an imidazole compound represented by the following structural formula (III):

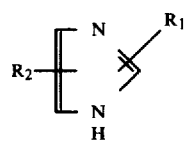

$$\text{(III)}$$

wherein $R_1$ and $R_2$ are as defined above.

As the halogenomethylstyrene to be used in the process of the present invention, there can be mentioned ortho, meta- and para-isomers of chloromethylstyrene, bromomethylstyrene and iodomethylstyrene. A commercially available mixture comprising meta-chloromethylstyrene and para-chloromethylstyrene at a meta/para ratio of 6/4 is preferably used.

As the imidazole compound that can be preferably used in the process of the present invention, there can be mentioned imidazole compounds of the formula (III) wherein $R_1$ and $R_2$ each independently stand for a hydrogen atom, a methyl group, an ethyl group, a normal propyl group, an isopropyl group, a phenyl group, a benzyl group, a pyridyl group or a nitro group, examples of which compounds include imidazole, 2-methylimidazole, 2-isopropylimidazole, 2-phenylimidazole, 2-pyridylimidazole, 2-ethyl-4(5)-methylimidazole, 2-isopropyl-4(5)-nitroimidazole, 4(5)-nitroimidazole and 2-methyl-4(5)-nitroimidazole. 2-Undecylimidazole and 2-heptadecylimidazole can also be preferably used. Especially preferred are imidazole, 2-methylimidazole, 2-ethyl-4(5)-methylimidazole, 2-nitroimidazole and 2-pyridylimidazole. 4-Substituted imidazole compounds can be 5-substituted imidazole compounds because of tautomerization. For example,

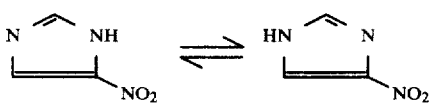

(5-nitroimidazole)　　　(4-nitroimidazole).

Therefore, 4-nitroimidazole and 5-nitroimidazole cannot be isolated from each other under normal conditions, and, hence, the name of the compound is described as 4(5)-nitroimidazole.

The reaction involved in the process of the present invention may be carried out either in the absence of or in the presence of an inert solvent. As the inert solvent, there can be mentioned, for example, water; aliphatic hydrocarbons such as n-pentane, n-hexane, n-heptane and n-octane; alcohols such as methanol, ethanol and isopropyl alcohol; ketones such as acetone, methyl ethyl ketone and diethyl ketone; ethers such as diethyl ether, methyl ethyl ether, dibutyl ethers, dioxane and tetrahydrofuran; aromatic hydrocarbons such as benzene, toluene and xylenes; esters such as ethyl formate, ethyl acetate and butyl acetates; amides such as dimethyl formamide and dimethyl acetamide; halogenated aliphatic hydrocarbons such as chloroform, methylene chloride and dichloroethanes; halogenated aromatic hydrocarbons such as chlorobenzene; and sulfoxides such as dimethyl sulfoxide. They may be used either alone or in mixture. Preferred inert solvents are water, acetone, methanol, ethanol, diethyl ether, ethyl acetate, chloroform, dimethyl formamide and mixtures thereof.

The reaction may usually be carried out at a temperature of $-70°$ C. to $+80°$ C., preferably at $-50°$ C. to $+60°$ C., more preferably at $0°$ C. to $50°$ C. The reaction period of time is not critical, but the reaction may usually be carried out for 5 minutes to 100 hours, preferably for 1 to 50 hours, more preferably 6 to 24 hours.

If the reaction is carried out in the presence of at least one reaction promoter selected from inorganic alkaline compounds, organic basic compounds, metals and metal halides, the reaction time may be shortened and the yield of the intended compound of the formula (I) may be increased. Preferred examples of the reaction promotor include inorganic alkaline compounds such as sodium hydroxide, potassium hydroxide, sodium carbonate and sodium hydrogencarbonate; organic basic compounds such as diethylamine, triethylamine and pyridine; metals such as iron, copper and tin; and metal halides such as ferrous chloride, cuprous chloride, stannous chloride and aluminum chloride.

We have found that if the reaction involved in the process of the present invention is carried out in the presence of a polymerization inhibitor, a high reaction temperature and/or high concentrations of the reactants can be employed so that the rate of reaction can be high. As the polymerization inhibitor, there can be mentioned, for example, derivatives of phenol such as 2-tert-butyl-4-hydroxyanisole, 2,6-di-tert-butyl-4-methylphenol, 4,4'-thiobis(6-tert-butyl-3-methylphenol) and 4,4'-butylidenebis(6-tert-butyl-3-methylphenol); derivatives of hydroquinones such as tert-butylhydroquinone and 2,5-di-tert-butylhydroquinone; nitroso group- and/or hydroxylamino group-containing compounds such as n-butyl nitrite and ammonium salt of N-nitrosophenylhydroxylamine (cupferron); and organic halide compounds such as dibromobenzene and trichlorobenzene. They may be used either alone or in mixture.

The process for the synthesis of the basic compound of the formula (I) according to the present invention will now be described by way of example in more detail.

The charging molar ratio of an imidazole compound of the formula (III) to a halogenomethylstyrene of the formula (II) is in the range of from 0.1 to 20, preferably in the range of from 1 to 7. Even if a reaction promoter selected from inorganic alkaline compounds, organic basic compounds, metals and metal halides is not added to the reaction system, the reaction proceeds, but if such a reaction promotor is added, the reaction may proceed at an increased rate. Where an inorganic alkaline compound or an organic basic compound is used as the reaction promotor, the chemical equivalent ratio of the reaction promotor to the halogenomethylstyrene is usually in the range of from 0.2 to 20, preferably in the range of from 1 to 5. Where a metal or a metal halide is used as the reaction promotor, the molar ratio of the reaction promotor to the halogenomethylstyrene is in the range of from 0.001 to 10, preferably in the range of from 0.01 to 0.1. The addition of a polymerization inhibitor to the reaction system is not necessarily needed, but it is preferred that a polymerization inhibitor be added to the reaction system because the presence of the polymerization inhibitor inhibits or minimizes the advance of polymerization of the halogenomethylstyrene and/or the product and, hence, permits of a higher reaction temperature at which the reaction period of time may be shorter. An inert solvent may optionally be used in the reaction. If an inert solvent is used in the reaction, the amount of the inert solvent cannot be determined independently because the solubility of the halogenomethylstyrene and/or the imidazole compound in the solvent must be taken into consideration. It is preferred that the inert solvent be used at least in a minimum amount necessary for providing a homogeneous reaction system. The inert solvent is usually used in an amount of 0 to 1,000 liters, preferably 0 to 100 liters, per mole of the halogenomethylstyrene. The reaction temperature is usually in the range of from −70° C. to 80° C., preferably in the range of from −50° C. to 60° C., more preferably in the range of from 0° C. to 50° C. The reaction period of time is not critical, but since the reaction rate varies depending on the reaction temperature, the amount of the inert solvent if used, and the amount and kind of reaction promotor if used, and the like, it is preferred that the advance of the reaction be traced by sometimes determining the amount of the desired product formed by means of liquid chromatography or the like.

Recommendable procedures for practicing the process of the present invention are as follows.

The solution of the imidazole compound dissolved in the inert solvent is charged into a flask, and the reaction promotor and the polymerization inhibitor are then added to the solution. To the resulting mixture is added the halogenomethylstyrene with sufficient stirring. The advance of the reaction is traced by liquid chromatography or the like, and the reaction is usually stopped after confirmation of completion of the reaction. The desired product formed is isolated from the reaction mixture and purified according to a customary separation procedure such as extraction.

The basic compound of the formula (I) according to the present invention can advantageously be used, for example, as a curing agent for epoxy resins. It also can be used for copolymerization with other monomers to give various copolymers.

In accordance with the third aspect of the present invention, there is provided a linear homopolymer represented by the following structural formula (IV)

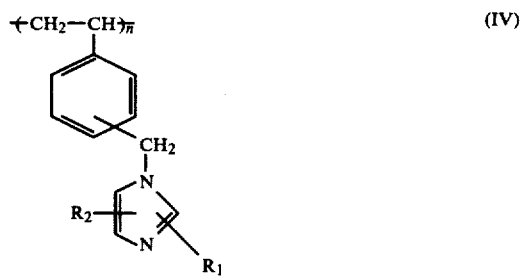

wherein $R_1$ and $R_2$ are as defined above.

In accordance with the fourth aspect of the present invention, there is provided a process for the preparation of a linear homopolymer of the formula (IV):

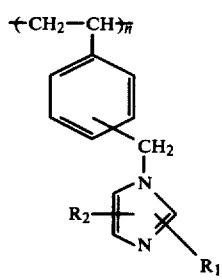

wherein $R_1$ and $R_2$ are as defined above, which comprises polymerizing a basic compound of the formula (I):

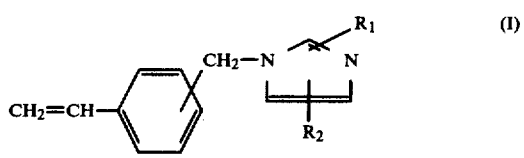

wherein $R_1$ and $R_2$ are as defined above.

For preparing a linear homopolymers of the formula (IV), any of the customary polymerization procedures can be employed. The compound of the formula (I) can be heat polymerized, but it may be preferred that a polymerization initiator be added.

As the polymerization initiator employed according to the present invention, there can be mentioned, for example, acyl peroxides, such as benzoyl peroxide and lauroyl peroxide, azonitriles, such as azobisisobutyronitrile and 2,2'-azobis(2,4-dimethylmaleronitrile), peroxides, such as ditert-butyl peroxide, dicumyl peroxide and methyl ethyl ketone peroxide, and hydroperoxides, such as cumenyl hydroperoxide and tertiary hydroperoxide.

Polymers according to the present invention may be produced by performing polymerization reaction either in the absence of or in the presence of an inert solvent. As the inert solvent, there can be mentioned, for example, aliphatic hydrocarbons such as n-pentane, n-hexane, n-heptane and n-octane; alcohols such as methanol, ethanol and isopropyl alcohol; ketones such as acetone, methyl ethyl ketone and diethyl ketone; ethers such as diethyl ether, methyl ethyl ether, dibutyl ethers, dioxane and tetrahydrofuran; aromatic hydrocarbons such as benzene, toluene and xylenes; esters such as ethyl formate, ethyl acetate and butyl acetates; amides such as dimethyl formamide and dimethyl acetamide; halogenated aliphatic hydrocarbons such as chloroform, methylene chloride and dichloroethanes; halogenated aromatic hydrocarbons such as chlorobenzene; and sulfoxides such as dimethyl sulfoxide. They may be used either alone or in mixture. Preferred inert solvent are water, acetone, methanol, ethanol, diethyl ether, ethyl acetate, chloroform, dimethyl formamide and mixtures thereof.

The reaction temperature is not critical, but the reaction may usually be carried out at a temperature of 20° to 120° C., preferably 60° to 100° C.

The homopolymer according to the present invention is useful as an extractant of metals and coating material. Surprisingly, the homopolymer according to the present invention has more adequate affinity to organic anions, such as alkylsulfonic acid, than the generally known basic polymers. Further, the linear homopolymer according to the present invention surprisingly has greater resistance to oxidation than the known amino group-containing polymers, such as polyvinylimidazole.

In accordance with the fifth aspect of the present invention, there is provided a linear copolymer comprising a structural unit of the formula (V) and a structural unit of the formula (VI):

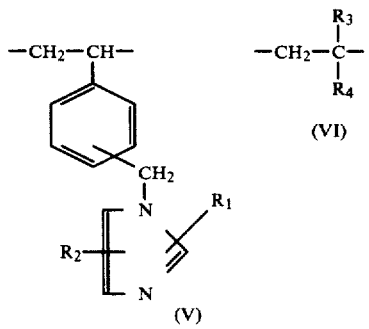

wherein
R$_1$ and R$_2$ are as defined above;
R$_3$ and R$_4$ each independently stand for a hydrogen atom, a halogen atom, a cyano group, an alkyl or alkenyl group having 1 to 5 carbon atoms, an aryl group, a halogenophenyl group, a phenyl group mono-, di- or tri-substituted with one or more substituents selected from C$_1$-C$_5$ straight chain or branched alkyl, haloalkyl, alkoxy and cyano groups, —COOA$_1$ in which A$_1$ represents a hydrogen atom or a C$_1$-C$_{10}$ hydrocarbon residue, —COA$_2$ in which A$_2$ represents a C$_1$-C$_{10}$ hydrocarbon residue, —OCOA$_3$ in which A$_3$ represents a C$_1$-C$_{10}$ hydrocarbon residue, —CONHA$_4$ in which A$_4$ represents a hydrogen atom or a C$_1$-C$_{10}$ hydrocarbon residue, an imidazolyl group, a pyridyl group or a carbozolyl group.

In accordance with the sixth aspect of the present invention, there is provided a process for the preparation of a linear copolymer comprising a structural unit of the formula (V) and a structural unit of the formula (VI):

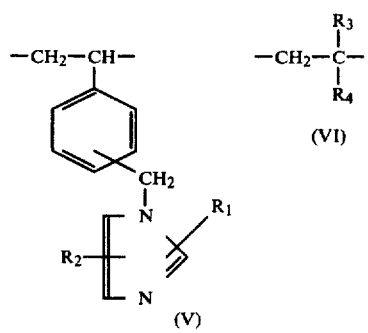

wherein R$_1$, R$_2$, R$_3$ and R$_4$ are as defined above, which comprises copolymerizing a basic compound of the formula (I):

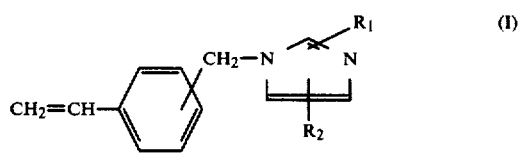

wherein R$_1$ and R$_2$ are as defined above, with a monomer of the formula (IX):

wherein R$_3$ and R$_4$ are as defined above.

In accordance with the seventh aspect of the present invention, there is provided a cross-linked copolymer comprising a structural unit of the formula (V) and either or both of the structural units of the formula (VII) and (VIII):

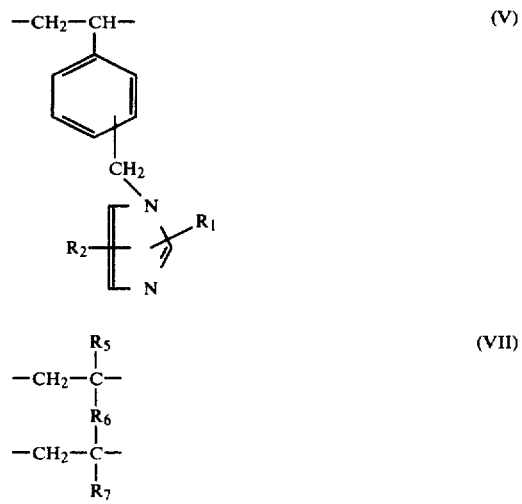

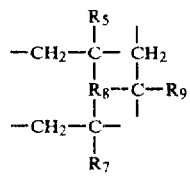

wherein:

$R_1$ and $R_2$ are as defined above, $R_5$, $R_7$ and $R_9$ each independently stand for a hydrogen atom or a methyl group; $R_6$ stands for

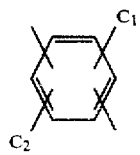

in which $C_1$ and $C_2$ each independently represent a hydrogen or a $C_1$–$C_5$ hydrocarbon residue,

in which $D_1$ represents —O—, —S—, —NH— or a $C_1$–$C_5$ alkylene group, —SO—, —CO—,

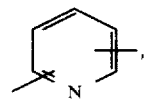

—CH$_2$—NH—CH$_2$—,

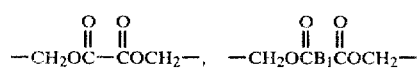

in which $B_1$ represents a divalent $C_1$–$C_8$ hydrocarbon residue,

in which $B_2$ represents a divalent $C_1$–$C_5$ hydrocarbon residue, $$-\overset{O}{\underset{\|}{C}}NH-B_3-NH\overset{O}{\underset{\|}{C}}-$$

in which $B_3$ represents a divalent $C_1$–$C_3$ hydrocarbon residue; and $R_8$ represents

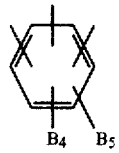

in which $B_4$ and $B_5$ each independently represents a $C_1$–$C_5$ hydrocarbon residue,

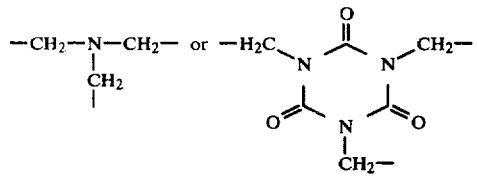

In accordance with the eighth aspect of the present invention, there is provided a process for the preparation of a cross-linked copolymer comprising a structural unit of the formula (V) and either or both of the structural units of the formula (VII) and (VIII):

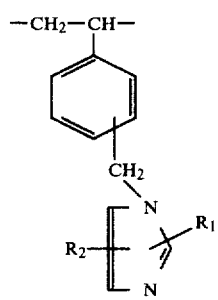  (V)

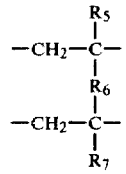  (VII)

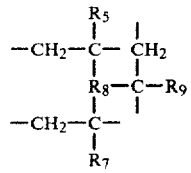  (VIII)

wherein $R_1$, $R_2$, $R_5$, $R_6$, $R_7$, $R_8$ and $R_9$ are as defined above, which comprises copolymerizing a basic compound of the formula (I):

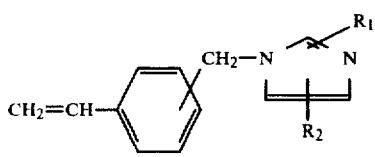  (I)

wherein $R_1$ and $R_2$ are as defined above, with at least one member selected from the group consisting of a monomer of the formula (X) and a monomer of the formula (XI):

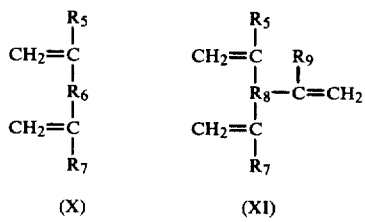

wherein $R_5$, $R_6$, $R_7$, $R_8$ and $R_9$ are as defined above.

In the structural unit of the formula (V), the imidazol-1-ylmethyl group may be located at the ortho-, meta- or pana-position relative to the vinyl moiety, but it is preferred that the group be located at the meta- or para-position. To obtain a preferred copolymer, $R_1$ and $R_2$ are expected to each independently stand for a hydrogen atom, a methyl group, an ethyl group, a benzyl group, a pyridyl group or a nitro group, and either $R_1$ or $R_2$ is expected to be located at the 2-position of the imidazole ring.

As the monomer of the formula (IX) employed in the process according to the present invention, there can be mentioned, for example, hydrocarbons, such as styrene, methylstyrene, diphenylethylene, ethylstyrene, dimethylstyrene, vinylnaphthalene, vinylphenanthrene, vinylmesitylene and 3,4,6-trimethylstyrene; styrene derivatives, such as chlorostyrene, methoxystyrene, bromostyrene, cyanostyrene, fluorostyrene, dichlorostyrene, chloromethylstyrene, trifluorostyrene and trifluoromethylstyrene; acrylonitriles, such as acrylonitrile, methacrylonitrile, and α-acetoxyacrylonitrile; acrylic acid, methacrylic acid; acrylates, such as methyl acrylate, lauryl acrylate, chloromethyl acrylate and ethyl acetoxylacrylate; methacrylates, such as cyclohexyl methacrylate; diethyl maleate, diethyl fumarate; vinyl ketones, such as methyl vinyl ketone and ethyl isopropenyl ketone; vinylidene compounds, such as vinylidene chloride, vinylidene bromide and vinylidene cyanide; acrylamides, such as acrylamide, methacrylamide and N-phenylacrylamide; esters of vinyl alcohol and aliphatic acid, such as vinyl acetate, vinyl butyrate and vinyl caprylate; and heterocyclic vinyl compounds, such as N-vinylcarbazole, vinylimidazole, methylvinylimidazole, vinylpyridine and methylvinylpyridine.

As preferred examples of $R_3$ and $R_4$, there can be mentioned a hydrogen atom, a cyano group, a chlorine atom, a methyl group, a phenyl group, a COOH group, a COOMe group, a COMe group, a OCOMe group and a CONH₂ group.

In the linear copolymer, the content ratio of the structural unit (V) to the structural unit (VI) may be optionally variable.

As the monomer of the formula (X) or (IX) employed in the process according to the present invention, there can be mentioned, for example, divinylbenzene, divinyltoluene, divinylxylene, divinylethylbenzene, trivinylbenzene, divinyldiphenyl, divinyldiphenylmethane, divinyldibenzyl, divinylphenyl ether, divinyldiphenyl sulfide, divinyldiphenylamine, divinyl sulfone, divinyl ketone, divinylpyridine, diallyl phthalate, diallyl maleate, diallyl fumarate, diallyl succinate, diallyl oxalate, diallyl adipate, diallyl sebacate, diallylamine, triallylamine, N,N'-ethylenediacrylamide, N,N'-methylenediacrylamide, N,N'-methylenedimethacrylamide, ethylene glycol dimethacrylate, ethylene glycol diacrylate, 1,3-butylene glycol diacrylate and triallyl isocyanurate. They may be used either alone or in mixture.

The copolymer comprising structural units (V) and (VII) and/or (VIII) according to the present invention may contain another type of structural unit in such an amount that will not adversely affect the properties of the crosslinked copolymer. Usually, such an additional structural unit may be added in an amount not exceeding 30% based on the total weight of the copolymer. Such an additional structural unit may be afforded by adding another monomer having an unsaturated group in the copolymerization reaction. The kind of the additional monomer is not critical. As the monomer additionally incorporated in the copolymerization according to the present invention, there can be mentioned, for example, hydrocarbons, such as styrene, methylstyrene, diphenylethylene, ethylstyrene, dimethylstyrene, vinylnaphthalene, vinylphenanthrene, vinylmesitylene, 3,4,6-trimethylstyrene, 1-vinyl-2-ethylacetylene, butadiene, isoprene and piperylene; styrene derivatives, such as chlorostyrene, methoxystyrene, bromostyrene, cyanostyrene, fluorostyrene, dichlorostyrene, chloromethylstyrene, trifluorostyrene, trifluoromethylstyrene, N,N-dimethylaminostyrene, nitrostyrene and aminostyrene; vinyl sulfides, such as methyl vinyl sulfide and phenyl vinyl sulfide; acrylonitriles, such as acrylonitrile, methacrylonitrile, and α-acetoxyacrylonitrile; acrylic acid, methacrylic acid; acrylates, such as methyl acrylate, lauryl acrylate, chloromethyl acrylate and ethyl acetoxylacrylate; methacrylates, such as cyclohexyl methacrylate, dimethylaminoethyl methacrylate, glusidyl methacrylate, tetrahydrofurfuryl methacrylate and hydroxyethyl methacrylate; diethyl maleate, diethyl fumarate; vinyl ketones, such as methyl vinyl ketone and ethyl isopropenyl ketone; vinylidene compounds, such as vinylidene chloride, vinylidene bromide and vinylidene cyanide; acrylamides, such as acrylamide, methacrylamide, N-phenylacrylamide, N-butoxymethylacrylamide, diacetonacrylamide and N,N-dimethylaminoethylacrylamide; esters of vinyl alcohol and aliphatic acid, such as vinyl acetate, vinyl butyrate and vinyl caprylate; thioesters, such as phenyl thiomethacrylate, methyl thioacrylate and vinyl thioacetate; and heterocyclic vinyl compounds, such as N-vinylsuccinimide, N-vinylpyrrolidone, N-vinylphthalimide, N-vinylcarbazole, vinylfuran, 2-vinylbenzofuran, vinylthiophene, vinylimidazole, methylvinylimidazole, vinylpyrazole, vinyl oxazolidone, vinylthiazole, vinyltetrazole, vinylpyridine, methylvinylpyridine, 2,4-dimethyl-6-vinyltriazine and vinylquinoline. In copolymerizing monomers (I) and (IX), (X) and/or (XI), any of the customary polymerization procedures can be employed. A mixture of such monomers can be heat polymerized, but it may be preferred that a polymerization initiator be added. As the polymerization initiator employed according to the present invention, there can be mentioned, for example, acyl peroxides, such as benzoyl peroxide and lauroyl peroxide, azonitriles, such as azobisisobutyronitrile and 2,2'-azobis(2,4-dimethylmaleronitrile), peroxides, such as ditert-butyl peroxide, dicumyl peroxide and methyl ethyl ketone peroxide, and hydroperoxides, such as cumenyl hydroperoxide and tertiary hydroperoxide.

Copolymers according to the present invention may be produced by performing copolymerization reaction either in the absence of or in the presence of an inert solvent. As the inert solvent, there can be mentioned, for example, aliphatic hydrocarbons such as n-pentane, n-hexane, n-heptane and n-octane; alcohols such as methanol, ethanol and isopropyl alcohol; ketons such as acetone, methyl ethyl ketone and diethyl ketone; ethers such as diethyl ether, methyl ethyl ether, dibutyl ethers, dioxane and tetrahydrofuran; aromatic hydrocarbons such as benzene, toluene and xylenes; esters such as ethyl formate, ethyl acetate and butyl acetates; amides such as dimethyl formamide and dimethyl acetamide; halogenated aliphatic hydrocarbons such as chloroform, methylene chloride and dichloroethanes; halogenated aromatic hydrocarbons such as chlorobenzene; and sulfoxides such as dimethyl sulfoxide. They may be used either alone or in mixture. The reaction temperature is not critical, but the reaction may usually be carried out at a temperature of 20° to 120° C., preferably 60° to 100° C.

In accordance with the ninth aspect of the present invention, there is provided a method of ion exchange which comprises contacting with an aqueous feric chloride solution a cross-linked copolymer comprising a structural unit of the formula (V) and either or both of the structural units of the formula (VII) and (VIII):

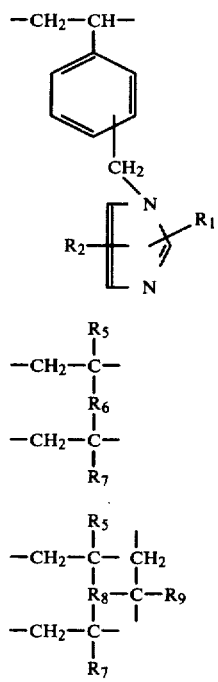

wherein $R_1$, $R_2$, $R_5$, $R_6$, $R_7$, $R_8$ and $R_9$ are as defined above.

Of the above-mentioned copolymers in the present invention, a three-dimensional cross-linked copolymer may be employed as an ion exchange resin by taking advantage of a basic property of the imidazole ring attached to the main chain as a side chain. Moreover, according to the present invention, it has been found that a linear copolymer in the present invention can be used as an extractant of metals, a sizing agent, an antistatic agent and the like. Furthermore, it has been surprisingly found that the copolymers in the present invention has an excellent resistance to oxidation as compared with the homologues. The copolymers in the present invention have showed a particularly excellent oxidation resistance to Fe(III) ion. The copolymers in the present invention have showed only a small degree of deterioration of performance, for example, when a cross-linked copolymer was used as an ion exchange resin in contact with Fe(III) ion and when a linear copolymer was used as an extractant of Fe(III) ion. In addition, the copolymers in the present invention also have showed an excellent oxidation resistance to ions such as $Cu^{2+}$, $MnO_4^{2+}$, $ClO_3^-$, $Sn^{4+}$, $UO_2^{2+}$, $PtCl_6^{2-}$, $Hg^{2+}$, $AuCl_4^-$, $Mn^{3+}$, $Ce^{4+}$ and $Pr^{4+}$.

The present invention will now be described in more detail with reference to the following Examples that by no means limit the scope of the invention.

EXAMPLE 1

A four-necked flask having a capacity of 1 liter and provided with a thermometer, a reflux condenser, a dropping funnel and a stirrer was charged with a solution of 136.2 g (2.0 moles) of imidazole in 500 ml of acetone, and 76.0 g (0.5 mole) of m-chloromethylstyrene was added dropwise to the solution under agitation from the dropping funnel over a period of about 30 minutes while maintaining the inner temperature at 40° C. Then, agitation was continued at this temperature for about 16 hours. The acetone was removed from the reacton mixture by distillation, and the residue was dissolved in 500 ml of ether. The solution was washed with 50 ml of water six times, whereby the unreacted imidazole was completely removed. Then, 100 ml of a 2 N aqueous solution of hydrochloric acid was added to the ether solution, and a part of the product was back-extracted in the form of the hydrochloride. This back extraction was repeated three times. When 200 ml of a 4 N aqueous solution of sodium hydroxide was added to the hydrochloric acid solution, the reaction product was separated in the form of oil drops. The product was recovered by conducting extraction using 50 ml of ether three times. The recovered product was dried with anhydrous sodium sulfate, and the distillation-removal of ether gave 77.3 g of a substantially colorless liquid (yield: 84%).

Results of the analysis by liquid chromatography of the product indicated that the product was a single substance. From results of spectroanalysis and other ordinary organic chemical analysis methods, it was determined that this single substance was m-(1-imidazolylmethyl)styrene.

The analysis results are as follows:

Elementary analysis: C, 78.39 (78.23); H, 6.60 (6.57); N, 15.01 (15.20). Each parenthesized figure shows a theoretical value.

Mass spectrum: 184 (M+/e), 157 (M-$C_2H_3$), 117 (M-$C_3H_3N_2$), 103 ($C_8$7), 81 (M-$C_8H_7$), 76 ($C_6H_4$), 67 ($C_3H_3N_2$). M indicates the parent peak.

Infrared absorption spectrum (cm$^{-1}$): 712, 850, 905, 1078, 1106, 1230, 1275, 1438, 1501, 1601, 1628, 2950, etc.

Nuclear magnetic resonance spectrum (CDCl$_3$, TMS-standard, δ-value): 6.4–7.6 (multiplet, 8H), 5.66 (doublet, 1H), 5,26 (doublet, 1H), 4.80 (singlet, 2H).

The form of peak and the area of peak are shown in parentheses.

2.0 g of m-(1-imidazolylmethyl)styrene so obtained was added to and mixed with a solution of 6.0 g of a bisphenol A-epichlorohydrin epoxy resin (epoxy equivalent: 190) in 7.3 g of ethyl cellosolve. The resulting mixture was coated by a bar coater on an iron plate treated with zinc phosphate, and heated at 150° C. for 1 hour. The epoxy resin was completely cured. The physical properties of the cured film of the epoxy resin are as follows.

Film Thickness: 30μ
Pencil Hardness (JIS K 2400-1979): 3 H
Flexibility (JIS K 2400-1979): >10 mm
Erichsen Cupping Test (A method) (JIS Z 2247-1977): 5.7 mm
Impact Resistance (B method) (JIS K 2400-1979):
 ¼ inch×500 g, 30 cm pass
 ½ inch×500 g, 50 cm pass

EXAMPLE 2

A four-necked flask having a capacity of 1 liter and provided with a thermometer, a reflux condenser, a dropping funnel and a stirrer was charged with 76.0 g (0.5 mole) of chloromethylstyrene (a mixture of 60% of the meta-isomer and 40% of the para-isomer), and 1.0 g of p-tert-butylcatechol was then added, followed by elevating the inner temperature up to 40° C. To the resultant was added 136.2 g (2 moles) of imidazole, followed by agitation. When agitation was continued for about 30 minutes while maintaining the inner temperature at 40° C., there was obtained a homogeneous liquid. Stirring was further continued at this temperature for about 20 hours. The reaction mixture thus obtained was dissolved in 500 ml of ether. The reaction product was isolated and purified in the same manner as described in Example 1 to obtain 60.2 g of a colorless liquid (yield: 65%).

By the liquid chromatography analysis, it was found that the liquid was a mixture of two substances and the amount ratio of the two substances was 3/2, which was the same as the meta/para ratio in the starting chloromethylstyrene. By spectroanalysis and other ordinary organic chemical analysis methods, it was determined that the two substances were m-(1-imidazolylmethyl)styrene and p-(1-imidazolylmethyl)styrene.

The analysis results are as follows:

Elementary analysis: C, 78.12 (78.23); H, 6.51 (6.57); N, 15.37 (15.20). Each parenthesized figure shows a theoretical value.

Mass spectrum: 184 (M+/e), 157 (M-$C_2H_3$), 117 (M-$C_3H_3N_2$), 103 ($C_8H_7$), 81 (M-$C_8H_7$), 76 ($C_6H_4$), 67 ($C_3H_3N_2$). M indicates the parent peak.

Infrared absorption spectrum (cm$^{-1}$): 712, 815, 905, 1030, 1078, 1106, 1230, 1275, 1408, 1438, 1501, 1601, 1628, 2950, etc.

Nuclear magnetic resonance spectrum (CDCl$_3$, TMS-standard, δ-value): 6.4–7.6 (multiplet, 8H), 5.66 (doublet, 1H), 5.26 (doublet, 1H), 4.80 (singlet, 2H).

The refractive index ($n_D$) of the mixture of the two substances was 1.5477 and the freezing point (fp) of the mixture was −8° to −24° C. When the double bond was determined by using mercury acetate, it was found that the amount of the double bond was 5.38 millimoles/g (the theoretical value being 5.43 millimoles/g).

EXAMPLE 3

A 4-necked flask having a capacity of 200 ml and provided with a thermometer, a reflux condenser, a dropping funnel and a stirrer was charged with a solution of 5.25 g (0.0625 mole) of sodium hydrogencarbonate in a liquid mixture of 50 ml of water and 50 ml of acetone. Then, 0.05 g of p-tert-butylcatechol was added to the solution and 13.6 g (0.2 mole) of imidazole was added. Then, from the dropping funnel, 7.6 g (0.05 mole) of p-chloromethylstyrene was added dropwise to the mixture over a period of about 10 minutes. Then, the temperature was elevated to 50° C. and the mixture was stirred for 20 hours. The reaction product was recovered by filtration, and isolated and purified in the same manner as described in Example 1 to obtain 8.1 g of a substantially colorless liquid (yield: 88%).

Results of the analysis by liquid chromatography indicated that the product was a single substance. From the results of spectroanalysis and other ordinary organic chemical analysis methods, it was determined that this single substance was p-(1-imidazolylmethyl)styrene.

The analysis results are as follows:

Elementary analysis: C, 78.19 (78.23); H, 6.66 (6.57); N, 15.15 (15.20). Each parenthesized figure shows a theoretical value.

Mass spectrum: 184 (M+/e), 157 (M-$C_2H_3$), 117 (M-$C_3H_3N_2$), 103 ($C_8H_7$), 81 (M-$C_8H_7$), 76 ($C_6H_4$), 67 ($C_3H_3N_2$).

Infrared absorption spectrum (cm$^{-1}$): 821, 1030, 1106, 1230, 1275, 1408, 1501, 1601, 1628, 2950, etc.

Nuclear magnetic resonance spectrum (CDCl$_3$, TMS-standard, δ-value): 6.4–7.6 (multiplet, 8H), 5.66 (doublet, 1H), 5.26 (doublet 1H), 4.80 (singlet, 2H).

EXAMPLE 4

A 200 ml-capacity 3-necked flask equipped with a thermometer, a reflux condenser and a stirrer was charged with a solution of 0.05 g of 4,4'-thiobis(6-tert-butyl-3-methylphenol) and 6.81 g (0.10 mole) of imidazole in a liquid mixture of 50 ml of acetone and 50 ml of water, and 0.5 g (0.005 mole) of cuprous chloride was further added. Then, 7.6 g (0.050 mole) of chloromethylstyrene (a mixture of 60% of the meta-isomer and 40% of the para-isomer) was added to the solution under agitation while maintaining the inner temperature at 40° C. The mixture was stirred for about 8 hours while maintaining the inner temperature at 40° C. The reaction product was recovered by filtration, and isolated and purified in the same manner as described in Example 1 to obtain 8.46 g of a colorless liquid (yield: 92%).

From the results of liquid chromatography and other ordinary organic chemical analysis methods, it was found that the product was the same substance as obtained in Example 2.

EXAMPLE 5

A 500 ml-capacity 3-necked flask equipped with a thermometer, a reflux condenser and a stirrer was charged with 106.5 g (0.70 mole) of chloromethylstyrene (a mixture of 60% of the meta-isomer and 40% of the para-isomer) and 210.7 g (2.57 moles) of 2-methylimidazole, and a solution of 1.2 g of p-tert-butylcatechol in 120 ml of acetone was then added. When stirring was continued at a reaction temperature maintained at 40° C. for about 30 minutes, the reaction mixture became homogeneous, and the reaction was then continued for 6 hours. The conversion was higher than 98%. The acetone was removed from the reaction mixture by distillation, and the residue was treated in the same manner as in Example 1 to obtain 125.4 g of a colorless liquid (yield: 90%).

By the liquid chromatography analysis, it was found that the liquid was a mixture of two substances and the ratio of the two substances was 3/2, which was the same as the meta/para ratio in the starting chloromethylstyrene. By spectroanalysis and other ordinary organic chemical analysis methods, it was determined that the two substances were m-(2-methyl-imidazol-1-ylmethyl)styrene and p-(2-methylimidazol-1-ylmethyl)styrene.

The analysis results are as follows:

Elementary analysis: C, 78.68 (78.75); H, 7.10 (7.12); N, 14.22 (14.13). Each parenthesized figure shows a theoretical value.

Mass spectrum:

198 (M+/e), 171 (M-$C_2H_3$), 117 (M-$C_4H_5N_2$), 103 ($C_8H_7$), 95 (M-$C_8H_7$), 81 ($C_4H_5N_2$), 76 ($C_6H_4$). M indicates the parent peak.

Infrared absorption spectrum ($cm^{-1}$): 712, 821, 913, 1078, 1130, 1290, 1350, 1425, 1501, 1601, 1628, 2950, etc.

Nuclear magnetic resonance spectrum ($CDCl_3$, TMS-standard, δ-value): 6.4–7.6 (multiplet, 8H), 5.66 (doublet, 1H), 5.26 (doublet, 1H), 5.00 (singlet, 2H), 2.30 (singlet, 3H).

The refractive index ($n_D$) of the mixture of the two substances was 1.5817. When the double bond was determined by using mercury acetate, it was found that the amount of the doublet bond was 4.98 millimoles/g (the theoretical value being 5.05 millimoles/g).

EXAMPLE 6

A 200 ml-capacity 3-necked flask equipped with a thermometer, a reflux condenser and a stirring rod was charged with a solution of 0.05 g of 4,4'-thiobis(6-tert-butyl-3-methylphenol) and 8.21 g (0.10 mole) of 2-methylimidazole in 100 ml of methanol. Then, 3.5 g (0.0625 mole) of potassium hydroxide and 7.6 g (0.05 mole) of chloromethylstyrene (a mixture of 60% of the meta-isomer and 40% of the para-isomer) were added to the solution. The temperature was elevated to 40° C. and the reaction was carried out under agitation for 8 hours to obtain a reaction mixture. When the reaction mixture was analyzed by liquid chromatography, the conversion was 60% based on the chloromethylstyrene. This reaction mixture was treated in the same manner as described in Example 1 to obtain 4.97 g of a product (yield: 50%). Results of the analysis by liquid chromatography indicated that the product was the same as the product obtained in Example 5.

EXAMPLE 7

A 500 ml-capacity 3-necked flask equipped with a thermometer, a reflux condenser and a stirrer was charged with 106.5 g (0.70 mole) of chloromethylstyrene (a mixture of 60% of the meta-isomer and 40% of the para-isomer) and 210.7 g (2.57 moles) of 2-methylimidazole, and a solution of 1.2 g of p-tert-butylcatechol in 120 ml of chloroform was then added. When the reaction temperature was elevated to 40° C. and stirring was continued for about 30 minutes, the reaction mixture became homogeneous. When the reaction was then continued for 6 hours, the conversion was increased to 100%. Then, 50 ml of water was added to the reaction mixture and water washing was conducted five times, whereby the unreacted 2-methylimidazole was completely removed. To the recovered chloroform solution was added 100 ml of a 2 N aqueous solution of hydrochloric acid, and a part of the product was extracted in the form of the hydrochloride. This extraction operation was repeated four times, and there was obtained a hydrochloric acid solution containing the hydrochloride. When 100 ml of a 10 N aqueous solution of sodium hydroxide was added to the hydrochloric acid solution, the product was separated as an oil phase. The product was recovered by performing extraction with 50 ml of ether three times, and the product was dried with anhydrous sodium sulfate, and the ether was removed therefrom by distillation to obtain 96.5 g of a liquid (yield: 70%). When the product was analyzed by liquid chromatography, it was found that the product was the same as the product obtained in Example 5.

EXAMPLE 8

A 500 ml-capacity 3-necked flask equipped with a thermometer, a reflux condenser and a stirring rod was charged with a solution of 0.05 g of tert-butylhydroquinone and 22.2 g (0.1 mole) of 2-undecylimidazole in 400 ml of chloroform, and 0.5 g (0.0025 mole) of ferrous chloride and 7.6 g (0.050 mole) of p-chloromethylstyrene were then added to the solution. The mixture was stirred for 20 hours while maintaining the inner temperature at 45° C. The reaction product was isolated from the reaction mixture in the same manner as described in Example 7 to obtain 6.74 g of a colorless solid (yield: 40%). Results of the analyses indicated that the product was p-(2-undecylimidazol-1-ylmethyl)styrene.

The analysis results are as follows:

Elementary analysis: C, 81.76 (81.60); H, 10.03 (10.12); N, 8.21 (8.27). Each parenthesized figure shows a theoretical value.

Infrared absorption spectrum ($cm^{-1}$): 821, 1021, 1105, 1275, 1380, 1418, 1501, 1601, 1628, 2860, 2930, etc.

When the double bond was determined according to the mercury acetate method, it was found that the amount of the double bond was 2.95 millimoles/g (the theoretical value being 2.96 millimoles/g).

EXAMPLE 9

A 500 ml-capacity 3-necked flask equipped with a thermometer, a reflux condenser and a stirring rod was charged with 0.05 g of tert-butylhydroquinone, 6.32 g (0.0625 mole) of triethylamine, 45.9 g (0.15 mole) of 2-heptadecylimidazole and a solution of 7.6 g (0.050 mole) of m-chloromethylstyrene in 400 ml of chloroform. The mixture was stirred for 20 hours while maintaining the inner temperature at 45° C.

The product was separated and isolated in the same manner as described in Example 7 to obtain 15.2 g of colorless crystals (yield: 72%). Results of the analyses indicated that the product was m-(2-heptadecylimidazol-1-ylmethyl)styrene.

The analysis results are as follows:

Elementary analysis: C, 82.26 (82.40); H, 10.89 (10.97); N, 6.85 (6.63). Each parenthesized figure shows a theoretical value.

Infrared absorption spectrum ($cm^{-1}$): 712, 821, 913, 1060, 1078, 1106, 1275, 1475, 1501, 1601, 1628, 2850, 2950, etc.

It was found that the amount of the double bond was 2.33 millimoles/g (the theoretical value being 2.37 millimoles/g).

EXAMPLE 10

A 500 ml-capacity 3-necked flask equipped with a thermometer, a reflux condenser and a stirring rod was charged with a solution of 0.03 g of tert-butylhydroquinone and 9.8 g (0.07 mole) of 2-phenylimidazole in 400 ml of chloroform, and 3.89 g (0.02 mole) of p-bromomethylstyrene was then added to the solution. The mixture was stirred for 15 hours while maintaining the inner temperature at 45° C.

A reaction product was isolated from the reaction mixture in the same manner as described in Example 6 to obtain 1.57 g of a colorless solid (yield: 31%). Results of the analyses indicated that the product was p-(2-phenylimidazol-1-ylmethyl)styrene.

The analysis results are as follows:

Elementary analysis: C, 83.28 (83.05); H, 6.05 (6.19); N, 10.67 (10.76) Each parenthesized figure shows a theoretical value.

Infrared absorption spectrum (cm$^{-1}$): 821, 1021, 1104, 1221, 1325, 1438, 1601, 1627, 2850, etc.

Mass spectrum: 260 (M$^+$/e), 233 (M-$C_2H_3$), 157 (M-$C_8H_7$), 143 ($C_9H_7N_2$), 117 (M-$C_9H_7N_2$), 77 ($C_6H_5$), 76 ($C_6H_4$). M indicates the parent peak.

When the double bond of the product was determined, it was found that the amount of the double bond was 3.73 millimoles/g (the theoretical value being 3.85 millimoles/g).

EXAMPLE 11

A 200 ml-capacity 3-necked flask equipped with a thermometer, a reflux condenser and a stirring rod was charged with a solution of 0.025 g of p-tert-butylcatechol and 5.65 g (0.05 mole) of 4(5)-nitroimidazole in 100 ml of dimethyl formamide, and 5.26 g (0.0626 mole) of sodium hydrogencarbonate and 3.8 g (0.025 mole) of chloromethylstyrene (a mixture of 60% of the meta-isomer and 40% of the para-isomer) were added to the solution. When the mixture was stirred for 24 hours while maintaining the inner temperature at 45° C., the conversion was increased to 100%. The reaction mixture was subjected to filtration, and the dimethyl formamide was removed from the filtrate by distillation. The residue was dissolved in 100 ml of toluene, and 15 ml of a 1 N aqueous solution of hydrochloric acid was added to the toluene solution and the unreacted 4(5)-nitroimidazole was extracted in the form of the hydrochloride. When this extraction operation was repeated three times, the unreacted 4(5)-nitroimidazole was completely removed. The remaining toluene solution was dried with anhydrous sodium sulfate, and the toluene was removed by distillation to obtain 3.8 g of a liquid (yield: 66%). By liquid chromatography, it was found that this liquid was a mixture of two substances at a ratio of 3/2, which was the same as the meta/para ratio in the starting chloromethylstyrene. From results of spectroanalysis and other ordinary organic chemical analysis methods, it was determined that these two substances were m-(4(5)-nitroimidazol-1-ylmethyl)styrene and p-(4(5)-nitroimidazol-1-ylmethyl)styrene. In the nuclear magnetic resonance spectrum, there were observed two peaks of 8.01 (δ-value) and 7.76 (δ-value) in a higher magnetic field region than the regions of the peaks of m-(1-imidazolylmethyl)styrene and p-(1-imidazolylmethyl)styrene. These two peaks indicate protons at the 4- and 5-positions of the imidazole ring. The ratio of the two peaks was 6/1. From this result, it was found that the ratio of m-(4-nitroimidazol-1-ylmethyl)styrene/m-(5-nitroimidazol-1-ylmethyl)styrene/p-(4-nitroimidazol-1-ylmethyl)styrene/p-(5-nitroimidazol-1-ylmethyl)styrene was 0.51/0.09/0.34/0.06.

The analysis results are as follows:

Elementary analysis: C, 62.68 (62.87); H, 4.81 (4.84); N, 18.44 (18.33); O, 14.07 (13.96). Each parenthesized figure shows a theoretical value.

Mass spectrum: 229 (M$^+$/e), 202 (M-$C_2H_3$), 126 (M-$C_8H_7$), 117 (M-$C_3H_2N_3O_2$), 112 ($C_3H_2N_3O_2$), 76 ($C_6H_4$), 46 ($NO_2$). M indicates the parent peak.

Infrared absorption spectrum: 821, 1021, 1240, 1290, 1339, 1545, 1605, 1630, 2850, etc.

Nuclear magnetic resonance spectrum (CDCl$_3$, TMS-standard, δ-value): 6.4–8.1 (multiplet, 7H), 5.70 (doublet, 1H), 5.26 (doublet, 1H), 5.13 (singlet, 2H).

It was found that the refractive index (n$_D$) of the obtained mixture of the two substances was 1.6033. When the double bond of the product was determined, it was found that the amount of the double bond was 4.30 millimoles/g (the theoretical value being 4.37 millimoles/g).

EXAMPLE 12

A 100 ml-capacity 4-necked flask equipped with a thermometer, a reflux condenser, a dropping funnel and a stirrer was charged with a solution of 0.05 g of p-tert-butylcatechol and 22.0 g (0.2 mole) of 2-ethyl-4(5)-methylimidazole in 50 ml of acetone, and while maintaining the inner temperature at 40° C., 7.6 g (0.05 mole) of chloromethylstyrene (a mixture of 60% of the meta-isomer and 40% of the para-isomer) was added dropwise to the solution from the dropping funnel over a period of about 10 minutes. When agitation was continued at the same temperature for about 10 hours, the conversion was increased to 100%. The acetone was removed from the reaction mixture by distillation, and the product was isolated from the residue in the same manner as described in Example 1 to obtain 10.1 g of a liquid (yield: 90%). From the result of liquid chromatography, it was confirmed that the product was a mixture of two substances at a ratio of 3/2, which was the same as the meta/para ratio in the starting chloromethylstyrene. By spectroanalysis and other ordinary organic chemical analysis methods, it was determined that the two substances were m-(2-ethyl-4(5)-methylimidazol-1-ylmethyl)styrene and p-(2-ethyl-4(5)-methylimidazol-1-ylmethyl)styrene. Although the nuclear magnetic resonance spectrum was examined in the same manner as in Example 11, it was impossible to distinguish the peaks due to the protons at the 4- and 5-positions of the imidazole ring from the peaks due to aromatic protons or vinyl protons. Accordingly, the ratio of the 4-methylimidazoles/the 5-methylimidazoles could not be determined.

The analysis results are as follows:

Elementary analysis: C, 79.51 (79.60); H, 8.09 (8.02); N, 12.40 (12.38) Each parenthesized figure shows a theoretical value.

Mass spectrum: 226 (M$^+$/e), 211 (M-$CH_3$), 199 (M-$C_2H_3$), 197 (M-$C_2H_5$), 123 (M-$C_8H_7$), 117 ($C_9H_9$), 109 ($C_6H_9N_2$), 103 ($C_8H_7$), 76 ($C_6H_4$). M indicates the parent peak.

Infrared absorption spectrum: 712, 750, 913, 990, 1068, 1168, 1301, 1428, 1507, 1605, 1632, 2950, etc.

Nuclear magnetic resonance spectrum (CDCl$_3$, TMS-standard, δ-value). 6.4–7.6 (multiplet, 6H), 5.73 (doublet, 1H), 5.26 (doublet, 1H), 4.96 (singlet, 2H), 2.60 (quartet, 2H), 2.21 (singlet, 3H), 1.26 (triplet, 3H).

It was found that the refractive index (n$_D$) of the obtained mixture of the two substance was 1.5497. When the double bond of the product was determined, it was found that the amount of the double bond was 4.39 millimoles/g (the theoretical value being 4.42 millimoles/g).

EXAMPLE 13

An ampule having a capacity of 50 ml was charged with a solution of 10 g of imidazolylmethylstyrene (a mixture of 60% of the meta-isomer and 40% of the para-isomer) dissolved in 20 ml of methanol, and 0.1 g of azobisisobutyronitrile (AIBN) was added to the solution. After sufficiently shaking the ampule, the ampule was purged with nitrogen and sealed. Then the ampule was kept in a water bath maintained at 80° C. for 20 hours. Then the ampule was broken off and the contents were taken out into n-hexane, followed by filtration to obtain a precipitate. The precipitate was washed with n-hexane and dried to obtain 10.0 g of a white product.

The elementary analysis of the product thus obtained gave the following results.

C: 77.72(78.23), H: 6.68(6.57), N: 15.60(15.20) Each parenthesized figure shows a theoretical value.

Main absorption peaks in an infrared absorption spectrum of the product were as follows: 712, 815, 905, 1030, 1078, 1106, 1275, 1438, 1501, 1601, 2950 etc. (unit: $cm^{-1}$).

As is apparent from the main adsorption peaks, the absence of carbon-carbon double bond implied by the lacks of peaks near the frequency 1630 $cm^{-1}$ showed the formation of a polymer.

The limiting viscosity number $[\eta]$ of the obtained polymer was 0.60 at 25° C. in 2 N hydrochloric acid.

1 g of the polymer thus obtained and 0.676 g (2.5 mmoles) of ferric chloride ($FeCl_3.6H_2O$) were dissolved in 2 N hydrochloric acid to prepare a solution having a total volume of 50 ml. After the solution was extracted with five 50 ml portions of chloroform, the iron concentration of the aqueous phase was measured. As a result, the iron concentration was found to be 2 mmole/liter. Substantially the same procedures as mentioned above were repeated to prepare a solution of ferric chloride in hydrochloric acid except that the polymer was not added. Thus prepared solution was extracted with five 50 ml portions of chloroform. After extraction, the concentration of iron in the water phase was measured. As a result, the iron concentration was found to be 50 mmole/liter. The iron concentration was equal to the concentration before extraction. From the above results, it was found that the polymer can be used as an extractant of metals.

EXAMPLES 14 TO 22

In substantially the same manner as in Example 13, various kinds of linear homopolymers represented by the structural formula (IV) were synthesized. The materials, experimental conditions and the analysis results are summarized in Table 1.

TABLE 1

| Example No. | Compound (I) R1 | Compound (I) R2 | Ratio of isomers*5 | Weight (g) | Initiator | Inert solvent | Polymerization conditions Temperature (°C) × Time (hr) | Treatment*3 | Yield (%) | Viscosity*4 (η) | Elementary analysis Figure in parenthesis is a theoretical value | Main peaks in infrared absorption spectrum (cm⁻¹) |
|---|---|---|---|---|---|---|---|---|---|---|---|---|
| 14 | H | H | meta-isomer | 10 | AIBN, 0.1 g*1 | toluene | 80 × 5 | B | 98 | 0.63 (H) | C; 77.93 (78.23) H; 6.58 ( 6.57) N; 15.49 (15.20) | 712, 805, 905, 1078, 1105, 1230, 1275, 1438, 1501, 1601, 2950 |
| 15 | H | 2-Me | m/p 60/40 | 10 | AIBN, 0.1 g | none | 80 × 5 | A | 100 | 0.40 (H) | C; 78.65 (78.75) H; 70.9 ( 7.12) N; 14.26 (14.13) | 712, 815, 905, 1030, 1078, 1130, 1290, 1350, 1425, 1501, 1601, 2950 |
| 16 | H | 2-C11H23 | para-isomer | 10 | AIBN, 0.1 g | none | 80 × 7 | A | 100 | 0.03 (D) | C; 81.72 (81.60) H; 10.17 (10.12) N; 8.11 ( 8.27) | 821, 1021, 1105, 1275, 1380, 1418, 1501, 1601, 2860, 2930 |
| 17 | H | 2-C17H35 | meta-isomer | 10 | AIBN, 0.1 g | dimethyl sulfoxide | 80 × 7 | B | 96 | 0.04 (D) | C; 82.28 (82.40) H; 11.00 (10.77) N; 6.72 ( 6.63) | 712, 805, 905, 1078, 1275, 1475, 1501, 1601, 2950 |
| 18 | H | 2-Ph | para-isomer | 10 | BPO, 0.1 g*2 | none | 80 × 5 | A | 100 | 0.32 (H) | C; 83.21 (83.05) H; 6.21 ( 6.19) N; 10.58 (10.76) | 821, 1021, 1104, 1221, 1325, 1438, 1601, 2850 |
| 19 | 2-Et | 4(5)-Me | m/p 60/40 | 10 | BPO, 0.1 g | acetone | 40 × 24 | B | 95 | 0.28 (H) | C; 79.50 (79.60) H; 8.10 ( 8.02) N; 12.39 (12.38) | 712, 750, 913, 990, 1068, 1168, 1301, 1428, 1507, 1605, 2950 |
| 20 | 2-CH2Ph | 4(5)-Me | m/p 60/40 | 10 | AIBN, 0.1 g | none | 80 × 5 | A | 100 | 0.24 (H) | C; 83.51 (83.30) H; 7.02 ( 6.99) N; 9.47 ( 9.71) | 712, 730, 805, 905, 1078, 1106, 1230, 1275, 1438, 1501, 1601, 2950 |
| 21 | H | 4(5)-NO2 | m/p 60/40 | 10 | AIBN, 0.1 g | none | 80 × 5 | B | 100 | 0.21 (H) | C; 62.69 (62.87) H; 4.80 ( 4.48) N; 18.40 (18.33) O; 14.11 (13.96) | 821, 1021, 1220, 1325, 1341, 1540, 1601, 2850 |
| 22 | 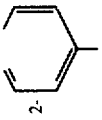 | 4(5)-Me | m/p 60/40 | 10 | AIBN, 0.1 g | acetone | 40 × 24 | B | 96 | 0.28 (H) | C; 78.46 (78.52) H; 6.14 ( 6.22) N; 15.38 (15.26) | 712, 805, 905, 990, 1030, 1078, 1106, 1150, 1230, 1275, 1438, 1501, 1601, 2950 |

*1 AIBN . . . azobisisobutyronitrile
*2 BPO . . . benzoyl peroxide
*3 Treatment A; Non-treatment B; Recovered from hexane
*4 (H): Dissolved in 2N hydrochloric acid (D): Dissolved in DMSO (dimethyl sulfoxide)
*5 m/p means meta-isomer/para-isomer
60/40 means 60/40

EXAMPLE 23

6.39 g of imidazolylmethylstyrene (a mixture of 60% of the meta-isomer and 40% of the para-isomer), 3.61 g of styrene and 0.1 g of azobisisobutyronitrile were placed in an ampule having a capacity of 30 ml. After sufficiently shaking the ampule, the ampule was purged with nitrogen and sealed. The ampule was then kept in a water bath maintained at 90° C. for 24 hours. Then the ampule was broken off and the solidified contents were taken out. With respect to the product thus obtained, elementary analysis and infrared analysis were carried out. The results are as follows:

Elementary analysis: C, 83.15(83.30); H, 7.00 (6.99); N, 9.85 (9.71). Each parenthesized figure shows a theoretical value.

Infrared absorption spectrum (cm$^{-1}$): 712, 815, 905, 1030, 1078, 1106, 1275, 1438, 1501, 1601, 2950, etc.

The obtained solid product amounted to 10.0 g (yield: 100%). When 0.5 g of the obtained solid product was mixed with 100 ml of 2 N hydrochloric acid, the product was completely dissolved in the hydrochloric acid solution and oily liquid did not appear on the surface of the hydrochloric acid solution at all.

Judging from both the infrared adsorption spectrum of the product which indicated the lacks of peaks due to the carbon-carbon double bond and the result of the above-mentioned dissolving test using a hydrochloric acid solution, the product was concluded to be an imidazolylmethylstyrene-styrene copolymer.

The limiting viscosity number [$\eta$] of the obtained polymer was 0.58 at 25° C. in 2 N hydrochloric acid.

1 g of the obtained copolymer and 0.270 g of ferric chloride (FeCl$_3$.6H$_2$O) were dissolved in 2 N hydrochloric acid to prepare a solution having a total volume of 50 ml. After the solution was extracted with five 50 ml portions of chloroform, the concentration of iron contained in the hydrochloric acid solution was measured. As a result, the iron concentration was found to be 1 mmole/liter. Substantially the same procedures as mentioned above were repeated to prepare a solution of ferric chloride in hydrochloric acid except that none of the polymer was added. Thus prepared solution was extracted with five 50 ml portions of chloroform. After extraction, the concentration of iron in the water phase was measured. As a result, the iron concentration was found to be 19 mmole/liter. The iron concentration was nearly equal to the concentration before extraction. From the above results, it was found that the polymer can be used as an extractant of metals.

EXAMPLES 24 TO 45

In substantially the same manner as in Example 23, using a monomer represented by the structural formula (I) and a monomer represented by the structural formula (IX), copolymerization was carried out. The materials, experimental conditions and the analysis results are summarized in Table 2.

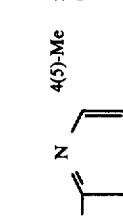

TABLE 2-continued

| Example No. | Compound (I) | | | Compound (IX) | | Initiator*1 | Inert solvent | Polymerization conditions Temperature (°C.) × Time (hr) | Treatment*2 | Yield (%) | Viscosity (η) | Elementary analysis Figure in parenthesis is a theoretical value | Main peaks in infrared absorption spectrum (cm$^{-1}$) |
|---|---|---|---|---|---|---|---|---|---|---|---|---|---|
| | $R_1$ | $R_2$ | Ratio of isomers*3 | Weight (g) | Compound name | Weight (g) | | | | | | | | |
| | | | | | | | | | | | | | 2950 |

*1Initiator
AIBN ... azobisisobutyronitrile
BPO ... benzoyl peroxide
*2Treatment
H; Dried after hexane washing
E; Dried after ether washing
W; Dried after water washing
*3Ratio of isomers
m/p 60/40 means meta-isomer/para-isomer = 60/40

EXAMPLE 46

An ampule having a capacity of 50 ml was charged with 7 g of imidazolylmethylstyrene (a mixture of 60% of the meta-isomer and 40% of the para-isomer), 3 g of m-divinylbenzene and 0.1 g of azobisisobutyronitrile. 10 g of toluene was added in the above obtained mixture and the resulting mixture was sufficiently shaken. After the ampule was sufficiently purged with nitrogen, the ampule was sealed and kept in a water bath maintained at 90° C. for 6 hours. The contents of the ampule completely solidified. The ampule was then broken off and the contents were taken out. Then, the product were crushed and pulverized in a morter. The pulverized product was washed with acetone and dried to obtain 10.0 g of the intended product. With respect to the product thus obtained, elementary analysis and infrared analysis were carried out. The results are as follows:

Elementary analysis: C, 82.6 (82.5); H, 6.5 (6.9); N, 10.9 (10.6). Each parenthesized figure shows a theoretical value.

Infrared absorption spectrum (cm$^{-1}$): 712, 815, 905, 1030, 1078, 1106, 1275, 1438, 1501, 1601, 2950, etc.

The obtained solid product was insoluble in acetone. The yield was 100%. In the infrared absorption spectrum, the peaks due to the carbon-carbon double bond of the monomer material disappeared. From the above-mentioned analysis, this product was concluded to be a m-divinylbenzeneimidazolylmethylstyrene cross-linked copolymer.

EXAMPLES 47 TO 69

In substantially the same manner as in Example 46, copolymerization was carried out using a monomer represented by the structural formula (I) and a monomer represented by the structural formula (X) or a monomer represented by the structural formula (XI). The materials, experimental conditions and the analysis results are summarized in Table 3.

TABLE 3

| Example No. | Compound (I) R₁ | R₂ | Ratio*2 of isomers | Other monomer Compound name | Weight (g) | Compound (X) or Compound (XI) Compound name | Weight (g) | Initiator | Inert solvent | Reaction conditions Temperature (°C) × Time (hr) | Treatment*1 | Yield (%) | Exchange capacity | Elementary analysis Figure in parenthesis is a theoretical value | Main peaks in infrared absorption spectrum (cm⁻¹) |
|---|---|---|---|---|---|---|---|---|---|---|---|---|---|---|---|
| 47 | H | H | m/p 60/40 | — | — | 56% divinylbenzene | 5 | AIBN 0.1 g | toluene | 90 × 5 | WA | 100 | 2.40 (2.47) | C; 84.87 (84.94) H; 7.43 (7.46) N; 7.70 (7.59) | 713, 815, 905, 1030, 1078, 1130, 1290, 1351, 1425, 1501, 1601, 2950 |
| 48 | H | H | m/p 60/40 | — | — | divinyl diphenyl amine | 4.45 | BPO 0.1 g | dimethyl sulfoxide | 90 × 24 | WA | 99 | 4.10 (4.25) | C; 82.04 (82.06) H; 6.65 (6.68) N; 11.31 (11.26) | 713, 815. 905, 1031, 1078, 1130, 1250, 1350, 1425, 1501, 1601, 2950 |
| 49 | H | 2-Me | m/p 60/40 | — | — | divinylphenyl ether | 5.29 | AIBN 0.1 g | none | 90 × 24 | WA | 98 | 2.18 (2.19) | C; 82.77 (82.82) H; 6.76 (6.71) N; 6.71 (6.66) O; 3.76 (3.80) | 712, 815, 905, 1031, 1078, 1130, 1250, 1350, 1425, 1501, 1601, 2950 |
| 50 | H | 2-C₁₁H₂₃ | m/p 60/40 | — | — | diallyl phthalate | 4.30 | AIBN 0.1 g | none | 90 × 24 | WA | 100 | 1.62 (1.64) | C; 79.90 (79.96) H; 8.90 (8.95) N; 5.30 (5.18) O; 5.90 (5.92) | 821, 1021, 1105, 1250, 1380, 1418, 1501, 1601, 1670, 2950 |
| 51 | H | 2-Me | m/p 60/40 | styrene | 7.17 | divinylbenzene (m/p = 60/40) | 1.57 | AIBN 0.1 g | benzoic ether | 90 × 5 | A | 100 | 3.20 (3.20) | C; 82.35 (82.57) H; 7.33 (7.29) N; 10.32 (10.14) | 712, 815, 905, 1030, 1078, 1130, 1290, 1350, 1425, 1501, 1601, 2950 |
| 52 | H | 2-C₁₁H₃₅ | meta-isomer | methyl vinyl ketone | 8.97 | trivinylbenzene | 0.17 | AIBN 0.1 g | none | 90 × 5 | A | 100 | 1.95 (1.97) | C; 82.82 (82.89) H; 10.38 (10.42) N; 6.00 (5.96) O; 0.80 (0.73) | 821, 1021, 1104, 1221, 1325, 1438, 1601, 1670, 2850 |
| 53 | H | 4(5)-NO₂ | m/p 60/40 | p-ethyl-styrene | 6.90 | divinyl detone | 0.88 | AIBN 0.1 g | none | 90 × 5 | A | 100 | 2.34 (2.59) | C; 71.25 (71.27) H; 5.91 (5.85) N; 12.11 (12.02) O; 10.72 (10.86) | 821, 1021, 1325, 1341, 1540, 1601, 1670, 2850 |
| 54 | H | 4(5)-Me | m/p 60/40 | dimethyl-styrene | 5.50 | N,N—ethylene-diacryl-amide | 2.52 | BPO 0.1 g | methanol | 70 × 24 | WA | 100 | 1.79 (1.86) | C; 75.34 (75.27) H; 7.37 (7.42) N; 12.60 (12.54) O; 4.69 (4.77) | 712, 805, 905, 990, 1030, 1078, 1106, 1150, 1230, 1438, 1601, 1660, 2950 |
| 55 | 2-Et | 4(5)-Me | para-isomer | — | — | triallyl isocyanurate | 4.23 | BPO 0.1 g | methanol | 70 × 24 | WA | 95 | 1.79 (1.86) | C; 70.38 (70.38) H; 7.15 (7.19) N; 14.33 (14.27) O; 8.13 (8.15) | 712, 750, 913, 990, 1068, 1168, 1301, 1428, 1507, 1605, 2950 |
| 56 | H | 2-Ph | para-isomer | acrylo-nitrile | 8.25 | divinyl-diphenyl | 1.19 | AIBN 0.1 g | none | 90 × 10 | WA | 100 | 2.82 (2.84) | C; 85.33 (85.53) H; 5.49 (5.44) N; 9.17 (9.03) | 821, 1021, 1104, 1221, 1325, 1438, 1601, 2240, 2850 |
| 57 | 2-CH₂Ph | 4(5)-Me | m/p 60/40 | methyl vinyl ketone | 8.85 | diallyl-amine | 0.67 | AIBN 0.1 g | none | 90 × 10 | WM | 100 | 2.87 (2.87) | C; 81.27 (81.34) H; 7.65 (7.63) N; 9.99 (9.93) O; 1.08 (1.10) | 712, 730, 805, 905, 1078, 1106, 1230, 1275, 1438, 1501, 1601, 1670, 2950 |
| 58 | 2-CH₂Ph | 4(5)-Me | m/p 60/40 | acryl-amide | 8.22 | ethylene glycol dimeth- | 1.15 | AIBN 0.1 g | none | 90 × 10 | WM | 100 | 2.68 (2.69) | C; 77.74 (77.88) H; 7.27 (7.25) N; 9.63 (9.56) | 712, 730, 805, 905, 1078, 1106, 1230, 1275, 1438, 1501, |

2- [pyridine ring structure with N]

TABLE 3-continued

| Example No. | Compound (I) R₁ | R₂ | Ratio*² of isomers | Other monomer Compound name | Weight (g) | Compound (X) or Compound (XI) Compound name | Weight (g) | Initiator | Inert solvent | Reaction conditions Temperature (°C.) × Time (hr) | Treatment*¹ | Yield (%) | Exchange capacity | Elementary analysis Figure in parenthesis is a theoretical value | Main peaks in infrared absorption spectrum (cm⁻¹) |
|---|---|---|---|---|---|---|---|---|---|---|---|---|---|---|---|
| 59 | 2-Et | 4(5)-Me | m/p 60/40 | butadiene | 7.31 | diallyl maleate acrylate | 2.11 | AIBN 0.1 g | none | 40 × 48 | WM | 100 | (2.80) | O; 5.36 (5.32) | 1600, 1670, 2950, 3400, 3500 |
| 60 | 2-Et | 4(5)-Me | m/p 60/40 | — | 5.46 | diallyl sebacate | 4.54 | AIBN 0.1 g | methanol | 90 × 10 | WA | 98 | (2.22) | C; 76.09 (76.26) H; 7.70 (7.81) N; 9.31 (9.04) O; 6.90 (6.89) | 712, 750, 913, 990, 1068, 1168, 1301, 1428, 1507, 1605, 1700, 2950 |
| 61 | 2-CH₂Ph | 4(5)-Me | m/p 60/40 | chloromethylstyrene | 7.62 | divinyl sulfone | 1.40 | AIBN 0.1 g | benzene | 90 × 24 | WA | 97 | (2.41) | C; 74.29 (74.36) H; 8.48 (8.59) N; 6.92 (6.76) O; 10.31 (10.29) | 712, 750, 913, 990, 1068, 1168, 1301, 1428, 1507, 1605, 1705, 2950 |
| 62 | 2-CH₂Ph | 4(5)-Me | m/p 60/40 | — | 6.87 | divinylpyridine | 3.13 | AIBN 0.1 g | methanol | 90 × 24 | WA | 100 | (4.07) | C; 77.08 (77.19) H; 6.52 (6.65) N; 7.54 (7.40) O; 2.82 (2.82) Cl; 3.33 (3.12) S; 2.71 (2.82) | 712, 730, 770, 805, 905, 1078, 1106, 1130, 1275, 1315, 1438, 1601, 2950 |
| 63 | 2-CH₂Ph | 4(5)-Me | m/p 60/40 | vinylidene chloride | 6.44 | divinyldibenzyl | 2.19 | AIBN 0.1 g | none | 90 × 24 | WA | 100 | (2.16) | C; 82.96 (83.02) H; 6.82 (6.97) N; 10.22 (10.02) | 712, 730, 805, 905, 1078, 1106, 1230, 1275, 1438, 1501, 1601, 2950 |
| 64 | 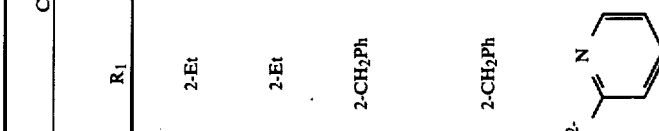 | 4(5)-Me | m/p 60/40 | — | 5.28 | diallyl phthalate | 4.72 | AIBN 0.1 g | benzoic methyl | 90 × 24 | WA | 100 | (1.79) | C; 73.72 (73.87) H; 6.25 (6.43) N; 10.02 (9.79) Cl; 10.01 (9.91) | 712, 805, 905, 990, 1030, 1078, 1106, 1150, 1230, 1601, 2950 |
| 65 | 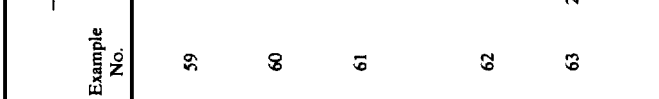 | H | m/p 60/40 | — | 8.44 | diallyl oxalate | 1.56 | AIBN 0.1 g | acetone | 60 × 24 | WA | 100 | 3.90 (3.92) | C; 73.12 (73.40) H; 6.34 (6.35) N; 8.31 (8.02) O; 12.23 (12.22) | 712, 805, 990, 1030, 1078, 1106, 1150, 1230, 1501, 1601, 1670, 2950 |
| 66 | H | H | | — | 8.70 | triarylamine | 1.30 | AIBN 0.1 g | dimethyl sulfoxide | 90 × 24 | WA | 100 | 3.98 (4.02) | C; 74.77 (74.84) H; 6.53 (6.47) N; 12.99 (12.83) O; 5.71 (5.86) | 712, 815, 905 1030, 1078, 1106, 1275, 1538, 1501, 1601, 1670, 2950 |
| 67 | H | H | | — | 8.06 | divinylphenylamine | 1.94 | AIBN 0.1 g | dimethyl sulfoxide | 90 × 24 | WA | 100 | 3.76 (3.77) | C; 78.69 (78.30) H; 7.00 (7.14) N; 14.31 (14.56) | 712, 815, 905, 925 1000, 1030, 1078, 1106, 1275, 1438, 1501, 1601, 2950 |
| 68 | H | 4(5)-Me | m/p 60/40 | — | 8.06 | divinylphenylsulfide | 1.94 | AIBN 0.1 g | none | 90 × 24 | WM | 97 | 3.54 (3.54) | C; 79.95 (79.90) H; 6.54 (6.62) N; 13.51 (13.49) | 712, 815, 905, 1030, 1078, 1106, 1275, 1438, 1490, 1501, 1601, 2950, 3400 |

TABLE 3-continued

| Example No. | Compound (I) | | | Other monomer | | Compound (X) or Compound (XI) | | | | Reaction conditions Temperature (°C.) × Time (hr) | Treatment[*1] | Yield (%) | Exchange capacity | Elementary analysis Figure in parenthesis is a theoretical value | Main peaks in infrared absorption spectrum (cm$^{-1}$) |
|---|---|---|---|---|---|---|---|---|---|---|---|---|---|---|---|
| | $R_1$ | $R_2$ | Ratio[*2] of isomers | Weight (g) | Compound name | Weight (g) | Compound name | Weight (g) | Initiator | Inert solvent | | | | | |
| 69 | H | 4(5)-Me | m/p 60/40 | 8.62 | — | — | divinyl-xylene | 1.38 | AIBN 0.1 g | toluene | 90 × 24 | W,A | 100 | 3.77 (3.75) | C; 80.71 (80.45) H; 7.01 (7.37) N; 12.28 (12.18) | 712, 815, 905, 1030, 1078, 1130, 1290, 1350, 1425, 1501, 1601, 2950 |

[*1]W—Washed with 1N HCl, 1N NaOH and then water
A—Washed with acetone
M—Washed with methanol
[*2]Ratio of isomers
m/p 60/40 means $\frac{\text{meta-isomer}}{\text{para-isomer}} = \frac{60}{40}$

EXAMPLE 70

A column was packed with 1 g of the copolymer obtained in Example 46 and then 100 ml of 1 N hydrochloric acid and 100 ml of acetone were passed through the column in sequence. Then, 100 ml of 1 N potassium nitrate was passed through the column, whereupon chlorine ion was no more detected in the effluent flowing from the column. In this case, $AgNO_3$ solution was used to detect chlorine ion. All the effluent that has flowed from the column after the potassium nitrate solution was supplied was collected and the total amount of chlorine ion was meassured. As a result, the total amount of chlorine ion was 3.80 mmoles. Then, 100 of 1 N hydrochloric acid and 100 ml of acetone was again supplied into the column in sequence. The copolymer was dried at 60° C. overnight and then its weight was measured. As a result, the copolymer weighed 1.13 g. From this result, this copolymer was found to have 3.36 meq of an exchange group per g of its dried hydrochloric acid type.

0.360 g of ferric chloride ($FeCl_3.6H_2O$) was dissolved in 2 N hydrochloric acid to prepare a solution having a total volume of 13.3 ml. 1 g of the above-obtained dry resin was added in the solution. Ultraviolet absorbances (350 nm) of the solution were measured before and after the addition of the dry resin to evaluate the change in concentration of iron contained in the solution. As a result, D-value (the ratio of the iron concentration of the resin phase to the iron concentration of the liquid phase) was found to be 80.

EXAMPLE 71

1 g of an imidazolylmethylstyrene polymer obtained in Example 13, 1 g of an imidazolylmethylstyrene-styrene copolymer obtained in Example 23, 1 g of polyvinylimidazol and 1 g of polyvinylpyridine were weighed out. To each weighed sample was added 40 ml of a ferric chloride solution having a concentration of 1 mole/liter. Then each sample was charged into each ampule and the ampules were sealed. These ampules were kept in an oil bath maintained at 180° C. for three days. Then the ampules were cooled to room temperature and the contents were taken out. In order to evaluate the amount of $Fe^{3+}$ consumed in the oxidation reaction, the concentration of $F^{3+}$ contained in each solution after the oxidation reaction was measured by means of potentiometry using an aqueous titanium trichloride solution. The results are given in Table 4.

TABLE 4

| | Amount of $Fe^{3+}$ before reaction [mmole] | Amount of $Fe^{3+}$ after reaction [mmole] | Amount of $Fe^{3+}$ consumed [mol]* |
|---|---|---|---|
| Polyimidazolylmethylstyrene | 40 | 28 | 2.2 |
| Imidazolylmethylstyrene-styrene copolymer | 40 | 33 | 2.0 |
| Polyvinylimidazol | 40 | 5 | 3.3 |
| Polyvinylpyridine | 40 | 1 or less | 4.2 |

Note:
*Number of moles of $Fe^{3+}$ consumed by one mole of each monomer having an amino group.

EXAMPLE 72

In a 20-ml ampule were charged 8 g of 4-vinylpyridine, 2 g of a commercially available divinylbenzene having a purity of 56% and 0.1 g of azobisisobutyromitrile (AIBN). In another 20-ml ampule were charged 8 g of vinylimidazole, 2 g of divinylbenzene and 0.1 g of azobisisobutyronitrile (AIBN). In still another 20-ml ampule were charged 8 g of (1-imidazolylmethyl)styrene (m/p=6/4), 2 g of divinylbenzene and 0.1 g of azobisisobutyronitrile (AIBN). These three ampules were then heat-sealed and shaken sufficiently. The ampules were kept in a water bath maintained at 80° C. to react for 16 hours. After completion of the reaction, the ampules were broken off to take out the reaction products. The reaction products were crushed and pulverized.

In order to evaluate oxidation resistance of the obtained three copolymers, in three 20-ml ampules was separately charged 1 g of each copolymer and added 20 ml of a 1 M ferric chloride solution. The ampules were sealed and allowed to stand at 180° C. for 3 days. After 3 days, the total exchange capacity of each copolymer was determined and compared with that determined before treating with a ferric chloride solution. The results are shown in Table 5.

TABLE 5

| | Total exchange capacity before treatment: $EC_0$ (meq.) | Total exchange capacity after treatment: $EC_1$ (meq.) | $\Delta EC^*$ |
|---|---|---|---|
| 4-vinylpyridine-divinylbenzene copolymer | 5.95 | 2.74 | 54 |
| 1-vinylimidazole-divinylbenzene copolymer | 6.49 | 4.02 | 38 |
| imidazolylmethyl-styrene-divinylbenzene copolymer | 3.74 | 3.18 | 15 |

Note:
*$\Delta EC$ is given by $\dfrac{EC_0 - EC_1}{EC_0} \times 100$

What is claimed is:

1. A basic compound represented by the following structural formula (I):

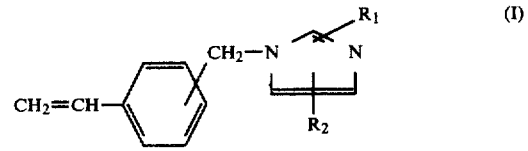

wherein $R_1$ and $R_2$ each independently stand for a hydrogen atom, a straight chain or branched alkyl group having 1 to 17 carbon atoms, a phenyl group unsubstituted or substituted with one or more substituents selected from $C_1$-$C_8$ straight chain or branched alkyl groups, halogen atoms and an amino group, a naphthyl group, an aralkyl group having as an alkyl moiety a $C_1$-$C_4$ straight chain or branched alkylene group and as an aryl moiety a phenyl group unsubstituted or substituted with one or more substituents selected from halogen atoms and an amino group, a pyridyl group unsubstituted or substituted with one or more substituents selected from $C_1-C_4$ straight chain or branched alkyl groups, halogen atoms and an amino group, or a nitro group.

2. A basic compound as claimed in claim 1, wherein $R_1$ and $R_2$ each independently stand for a hydrogen atom, a methyl group, an ethyl group, a normal propyl group, an isopropyl group, a phenyl group, a benzyl group, a pyridyl group or a nitro group.

3. A basic compound as claimed in claim 1, wherein the position of the imidazol-1-ylmethyl group relative to the vinyl group is the meta- or para-position.

4. A basic compound as claimed in claim 1, wherein $R_1$ is located at the 2-position of the imidazole ring.

5. A process for the preparation of a basic compound represented by the following structural formula (I):

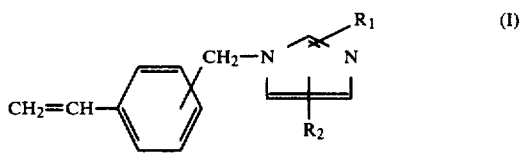

wherein $R_1$ and $R_2$ each independently stand for a hydrogen atom, a straight chain or branched alkyl group having 1 to 17 carbon atoms, a phenyl group unsubstituted or substituted with one or more substituents selected from $C_1-C_8$ straight chain or branched alkyl groups, halogen atoms and an amino group, a naphthyl group, an aralkyl group having as an alkyl moiety a $C_1-C_4$ straight chain or branched alkylene group and as an aryl moiety a phenyl group unsubstituted or substituted with one or more substituents selected from halogen atoms and an amino group, a pyridyl group unsubstituted or substituted with one or more substituents selected from $C_1-C_4$ straigth chain or branched alkyl groups, halogen atoms and an amino group, or a nitro group;
which comprises reacting a halogenomethylstyrene represented by the following structural formula (II):

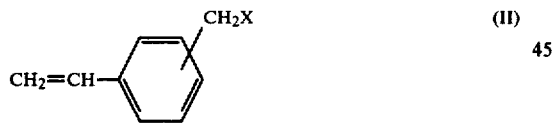

wherein X stands for Cl, Br or I,
with an imidazole compound represented by the following structural formula (III):

wherein $R_1$ and $R_2$ are as defined above.

6. A process according to claim 5, wherein the halogenomethylstyrene is m-chloromethylstyrene, p-chloromethylstyrene or a mixture of m-chloromethylstyrene and p-chloromethylstyrene.

7. A process according to claim 5, wherein the imidazole compound is one of the formula (III) wherein $R_1$ and $R_2$ each independently stand for a hydrogen atom, a methyl group, an ethyl group, a normal propyl group, an isopropyl group, a phenyl group, a benzyl group, a pyridyl group or a nitro group.

8. A process according to claim 5, wherein the reaction is carried out in the presence of an inert solvent.

9. A process according to claim 8, wherein the inert solvent is one member selected from the group consisting of water, acetone, methanol, ethanol, diethyl ether, ethyl acetate, chloroform, dimethyl formamide and mixtures thereof.

10. A process according to claim 5, wherein the reaction is carried out in the presence of at a temperature of $-70°$ C. to $+80°$ C.

11. A process according to claim 5, wherein the reaction is carried out in the presence of at least one reaction promoter selected from inorganic alkaline compounds, organic basic compounds, metals and metal halides.

12. A process according to claim 11, wherein the inorganic alkaline compounds are sodium hydroxide, potassium hydroxide, sodium carbonate and sodium hydrogencarbonate, the organic basic compounds are diethylamine, triethylamine and pyridine, the metals are iron, copper and tin, and the metal halides are ferrous chloride, cuprous chloride, stannous chloride and aluminum chloride.

13. A process according to claim 5, wherein the reaction is carried out in the presence of a polymerization inhibitor.

14. A process according to claim 13, wherein the polymerization inhibitor is selected from derivatives of phenol and derivatives of hydroquinone.

15. A linear homopolymer represented by the following structural formula (IV):

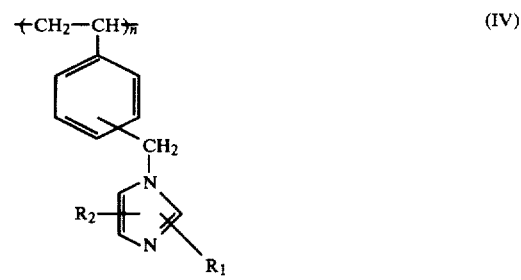

wherein $R_1$ and $R_2$ each independently stand for a hydrogen atom, a straight chain or branched alkyl group having 1 to 17 carbon atoms, a phenyl group unsubstituted or substituted with one or more substituents selected from $C_1-C_8$ straight chain or branched alkyl groups, halogen atoms and an amino group, a naphthyl group, an aralkyl group having as an alkyl moiety a $C_1-C_4$ straight chain or branched alkylene group and as an aryl moiety a phenyl group unsubstituted or substituted with one or more substituents selected from halogen atoms and an amino group, pyridyl group unsubstituted or substituted with one or more substituents selected from $C_1-C_4$ straight chain or branched alkyl groups, halogen atoms and an amino group, or a nitro group.

16. A linear homopolymer according to claim 15, wherein $R_1$ and $R_2$ each independently stand for a hydrogen atom, a methyl group, an ethyl group, a normal propyl group, an isopropyl group, a phenyl group, a benzyl group, a pyridyl group or a nitro group.

17. A linear homopolymer according to claim 15, wherein the position of the imidazol-1-ylmethyl group relative to the vinyl group is the meta- or para-position.

18. A linear homopolymer according to claim 15, wherein $R_1$ is located at the 2-position of the imidazole ring.

19. A process for the preparation of a linear homopolymer of the formula (IV):

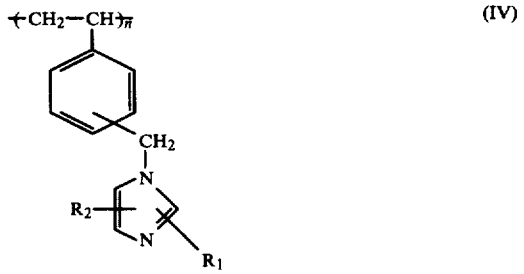

wherein $R_1$ and $R_2$ each independently stand for a hydrogen atom, a straight chain or branched alkyl group having 1 to 17 carbon atoms, a phenyl group unsubstituted or substituted with one or more substituents selected from $C_1$-$C_8$ straight chain or branched alkyl groups, halogen atoms and an amino group, a naphthyl group, an aralkyl group having as an alkyl moiety a $C_1$-$C_4$ straight chain or branched alkylene group and as an aryl moiety a phenyl group unsubstituted or substituted with one or more substituents selected from halogen atoms and an amino group, a pyridyl group unsubstituted or substituted with one or more substituents selected from $C_1$-$C_4$ straight chain or branched alkyl groups, halogen atoms and an amino group, or a nitro group;

which comprises polymerizing a basic compound of the formula (I):

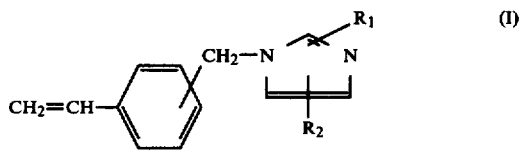

wherein $R_1$ and $R_2$ are as defined above.

20. A process according to claim 19, wherein the polymerization is performed in the presence of a polymerization initiator.

21. A process according to claim 19, wherein the polymerization is performed in the presence of an inert solvent.

22. A linear copolymer consisting of a structural unit of the formula (V) and a structural unit of the formula (VI):

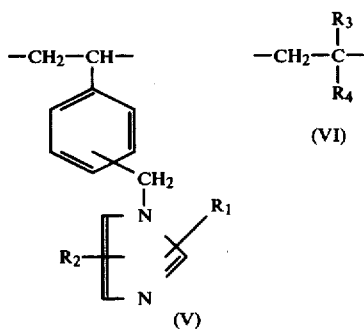

wherein $R_1$ and $R_2$ each independently stand for a hydrogen atom, a straight chain or branched alkyl group having 1 to 17 carbon atoms, a phenyl group unsubstituted or substituted with one or more substituents selected from $C_1$-$C_8$ straight chain or branched alkyl groups, halogen atoms and an amino group, a naphthyl group, an aralkyl group having as an alkyl moiety a $C_1$-$C_4$ straight chain or branched alkylene group and as an aryl moiety a phenyl group unsubstituted or substituted with one or more substituents selected from halogen atoms and an amino group, a pyridyl group unsubstituted or substituted with one or more substituents selected from $C_1$-$C_4$ straight chain or branched alkyl groups, halogen atoms and an amino group, or a nitro group;

$R_3$ and $R_4$ each independently stand for a hydrogen atom, a halogen atom, a cyano group, an alkyl or alkenyl group having 1 to 5 carbon atoms, an aryl group, a halogenophenyl group, a phenyl group mono-, di- or tri-substituted with one or more substituents selected from $C_1$-$C_5$ straight chain or branched alkyl, haloalkyl, alkoxy and cyano groups, —COOA$_1$ in which A$_1$ represents a hydrogen atom or a $C_1$-$C_{10}$ hydrocarbon residue, —COA$_2$ in which A$_2$ represents a $C_1$-$C_{10}$ hydrocarbon residue, —OCOA$_3$ in which A$_3$ represents a $C_1$-$C_{10}$ hydrocarbon residue, —CONHA$_4$ in which A$_4$ represents a hydrogen atom or a $C_1$-$C_{10}$ hydrocarbon residue, an imidazolyl group, a pyridyl group or a carbazolyl group.

23. A linear copolymer according to claim 22, wherein the position of the imidazol-1-ylmethyl group relative to the vinyl moiety in the structural unit of the formula (V) is the meta- or para-position.

24. A linear copolymer according to claim 22, wherein $R_1$ and $R_2$ each independently stand for a hydrogen atom, a methyl group, an ethyl group, a benzyl group, a pyridyl group or a nitro group.

25. A linear copolymer according to claim 22, wherein either $R_1$ or $R_2$ is located at the 2-position of the imidazole ring.

26. A linear copolymer according to claim 22, wherein $R_3$ and $R_4$ each independently stand for a hydrogen atom, a cyano group, a chlorine atom, a methyl group, a phenyl group, —COOH, —COOMe, —COMe, —OCOMe or —CONH$_2$.

27. A cross-linked copolymer consisting of a structural unit of the formula (V) and either or both of the structural units of the formula (VII) and (VIII):

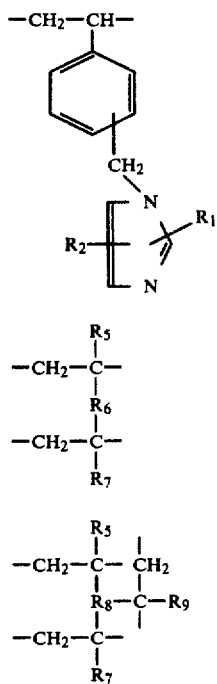 (V)

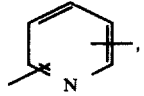 (VII)

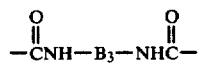 (VIII)

wherein
R$_1$ and R$_2$ each independently stand for a hydrogen atom, a straight chain or branched alkyl group having 1 to 17 carbon atoms, a phenyl group unsubstituted or substituted with one or more substituents selected from C$_1$–C$_8$ straight chain or branched alkyl groups, halogen atoms and an amino group, a naphthyl group, an aralkyl group having as an alkyl moiety a C$_1$–C$_4$ straight chain or branched alkylene group and as an aryl moiety a phenyl group unsubstituted or substituted with one or more substituents selected from halogen atoms and an amino group, a pyridyl group unsubstituted or substituted with one or more substituents selected from C$_1$–C$_4$ straight chain or branched alkyl groups, halogen atoms and an amino group, or a nitro group;

R$_5$, R$_7$ and R$_9$ each independently stand for a hydrogen atom or a methyl group;

R$_6$ stands for

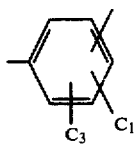

in which C$_1$ and C$_2$ each independently represent a hydrogen or a C$_1$–C$_5$ hydrocarbon residue,

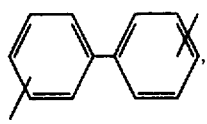

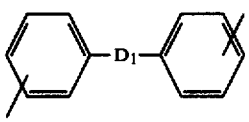

in which D$_1$ represents —O—, —S—, —NH— or a C$_1$–C$_5$ alkylene group,

—SO—, —CO—,

,

—CH$_2$—NH—CH$_2$—,

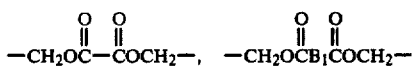

in which B$_1$ represents a divalent C$_1$–C$_8$ hydrocarbon residue, $$-COB_2OC-$$

in which B$_2$ represents a divalent C$_1$–C$_5$ hydrocarbon residue, or $$-\overset{O}{\underset{\|}{C}}NH-B_3-NH\overset{O}{\underset{\|}{C}}-$$

in which B$_3$ represents a divalent C$_1$–C$_3$ hydrocarbon residue;
and R$_8$ represents

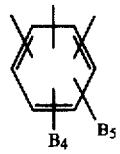

in which B$_4$ and B$_5$ each independently represent a C$_1$–C$_5$ hydrocarbon residue,

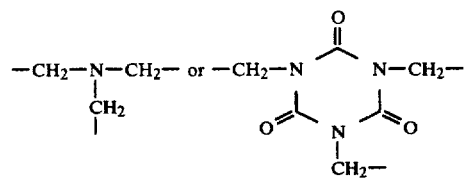

28. A cross-linked copolymer according to claim 27, wherein the position of the imidazol-1-ylmethyl group relative to the vinyl moiety in the structural unit of the formula (V) is the meta- or para-position.

29. A cross-linked copolymer according to claim 27, wherein R$_1$ and R$_2$ each independently stand for a hydrogen atom, a methyl group, an ethyl group, a benzyl group, a pyridyl group or a nitro group.

30. A cross-linked copolymer according to claim 27, wherein either R₁ or R₂ is located at the 2-position of the imidazole ring.

31. A cross-linked copolymer according to claim 27, wherein R₆ in the structural unit of the formula (VII) represents

32. A cross-linked copolymer according to claim 27, wherein R₆ in the structural unit of the formula (VII) represents

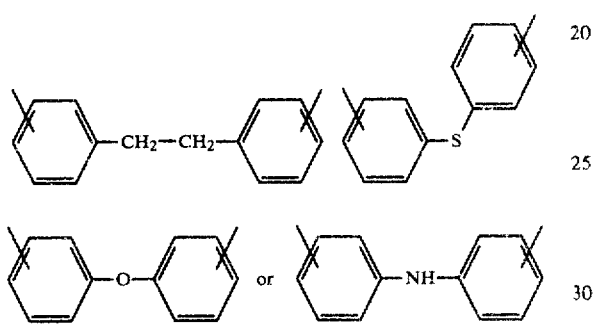

33. A cross-linked copolymer according to claim 27, wherein R₆ in the structural unit of the formula (VII) represents

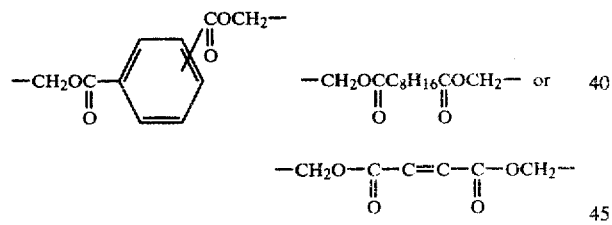

34. A cross-linked copolymer according to claim 27, wherein R₆ in the structural unit of the formula (VII) represents

35. A cross-linked copolymer according to claim 27, wherein R₆ in the structural unit of the formula (VII) represents

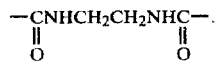

36. A cross-linked copolymer according to claim 27, which copolymer contains a structural unit of the formula (V) and a structural unit of the formula (VII) and/or a structura unit of the formula (VIII) in an amount of 70 to 100% based on the total weight of said copolymer.

37. A process for the preparation of a linear copolymer comprising a structural unit of the formula (V) and a structural unit of the formula (VI):

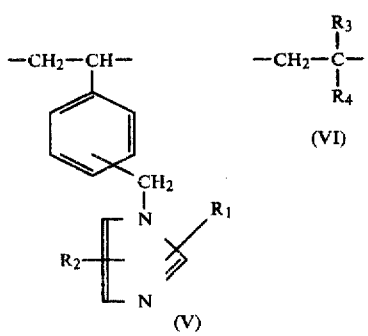

wherein
R₁ and R₂ each independently stand for a hydrogen atom, a straight chain or branched alkyl group having 1 to 17 carbon atoms, a phenyl group unsubstituted or substituted with one or more substituents selected from C₁-C₈ straight chain or branched alkyl groups, halogen atoms and an amino group, a naphthyl group, an aralkyl group having as an alkyl moiety a C₁-C₄ straight chain or branched alkylene group and as an aryl moiety a phenyl group unsubstituted or substituted with one or more substituents selected from halogen atoms and an amino group, a pyridyl group unsubstituted or substituted with one or more substituents selected from C₁-C₄ straight chain or branched alkyl groups, halogen atoms and an amino group, or a nitro group; and R₃ and R₄ each independently stand for a hydrogen atom, a halogen atom, a cyano group, an alkyl or alkenyl group having 1 to 5 carbon atoms, an aryl group, a halogenophenyl group, a phenyl group mono-, di- or tri-substituted with one or more substituents selected from C₁-C₅ straight chain or branched alkyl, haloalkyl, alkoxy and cyano groups, —COOA₁ in which A₁ represents a hydrogen atom or a C₁-C₁₀ hydrocarbon residue, —COA₂ in which A₂ represents a C₁-C₁₀ hydrocarbon residue, —OCOA₃ in which A₃ represents a C₁-C₁₀ hydrocarbon residue, —CONHA₄ in which A₄ represents a hydrogen atom or a C₁-C₁₀ hydrocarbon residue, an imidazolyl group, a pyridyl group or a carbazolyl group;

which comprises copolymerizing a basic compound of the formula (I):

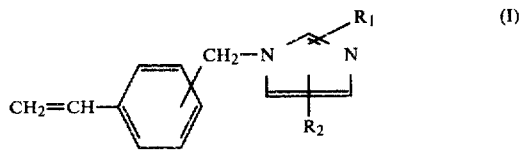

wherein R₁ and R₂ are as defined above, with a monomer of the formula (IX):

wherein $R_3$ and $R_4$ are as defined above.

38. A process according to claim 37, wherein the copolymerization is performed in the presence of a polymerization initiator.

39. A process according to claim 37, wherein the copolymerization is performed in the presence of an inert solvent.

40. A process for the preparation of a cross-linked copolymer consisting of a structural unit of the formula(V), and either or both of the structural units of the formula (VII) and (VIII):

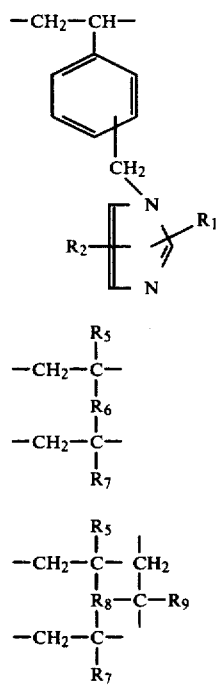

wherein
  $R_1$ and $R_2$ each independently stand for a hydrogen atom, a straight chain or branched alkyl group having 1 to 17 carbon atoms, a phenyl group unsubstituted or substituted with one or more substituents selected from $C_1$-$C_8$ straight chain or branched alkyl groups, halogen atoms and an amino group, a naphthyl group, an aralkyl group having as an alkyl moiety a $C_1$-$C_4$ straight chain or branched alkylene group and as an aryl moiety a phenyl group unsubstituted or substituted with one or more substituents selected from halogen atoms and an amino group, a pyridyl group unsubstituted or substituted with one or more substituents selected from $C_1$-$C_4$ straight chain or branched alkyl groups, halogen atoms and an amino group, or a nitro group;
  $R_5$, $R_7$ and $R_9$ each independently stand for a hydrogen atom or a methyl group;
  $R_6$ stands for

-continued

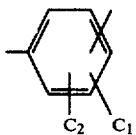

in which $C_1$ and $C_2$ each independently represent a $C_1$-$C_5$ hydrocarbon residue,

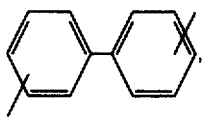

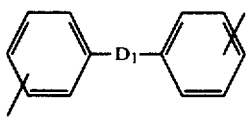

in which $D_1$ represents —O—, —S—, —NH— or a $C_1$-$C_5$ alkylene group, —SO—, —CO—,

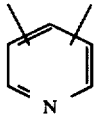

—$CH_2$—NH—$CH_2$—,

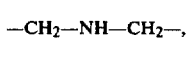 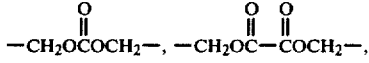

in which $B_1$ represents a divalent $C_1$-$C_8$ hydrocarbon residue,

in which $B_2$ represents a divalent $C_1$-$C_5$ hydrocarbon residue, or

in which $B_3$ represents a divalent $C_1$-$C_3$ hydrocarbon residue;
and $R_8$ represents

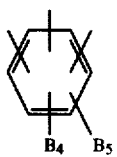

in which $B_4$ and $B_5$ each independently represents a $C_1$-$C_5$ hydrocarbon residue,

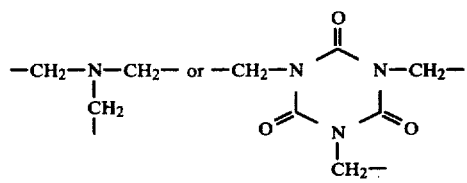

which comprises copolymerizing a basic compound of the formula (I):

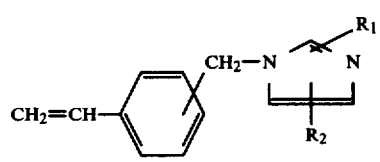

wherein $R_1$ and $R_2$ are as defined above, with at least one monomer selected from the group consisting of a monomer of the formula (X) and a monomer of the formula (XI):

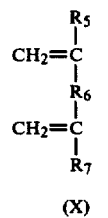    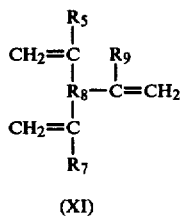

(X)       (XI)

wherein $R_5$, $R_6$, $R_7$, $R_8$ and $R_9$ are as defined above.

41. A process according to claim 40, wherein the copolymerization is performed in the presence of a polymerization initiator.

42. A process according to claim 40, wherein the copolymerization is performed in the presence of an inert solvent.

43. A method of ion exchange which comprises contacting with an aqueous ferric chloride solution a crosslinked copolymer consisting of a structural unit of the formula(V), and either or both of the structural units of the formula(VII) and (VIII):

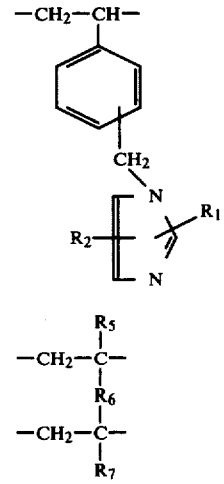

(V)

(VII)

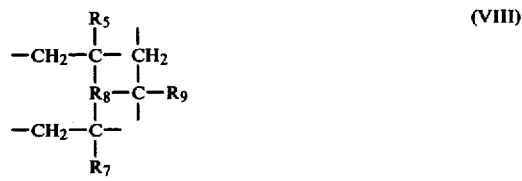

(VIII)

wherein $R_1$ and $R_2$ each independently stand for a hydrogen atom, a straight chain or branched alkyl group having 1 to 17 carbon atoms, a phenyl group unsubstituted or substituted with one or more substituents selected from $C_1$-$C_8$ straight chain or branched alkyl groups, halogen atoms and an amino group, a naphthyl group, an aralkyl group having as an alkyl moiety a $C_1$-$C_4$ straight chain or branched alkylene group and as an aryl moiety a phenyl group unsubstituted or substituted with one or more substituents selected from halogen atoms and an amino group, a pyridyl group unsubstituted or substituted with one or more substituents selected from $C_1$-$C_4$ straight chain or branched alkyl groups, halogen atoms and an amino group, or a nitro group;

$R_5$, $R_7$ and $R_9$ each independently stand for a hydrogen atom or a methyl group;

$R_6$ stands for

in which $C_1$ and $C_2$ each independently represent a $C_1$-$C_5$ hydrocarbon residue,

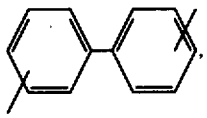

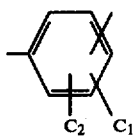

in which $D_1$ represents —O—, —S—, —NH— or a $C_1$-$C_5$ alkylane group,

—SO—, —CO—,

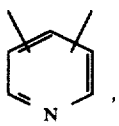

$-CH_2-NH-CH_2-$,

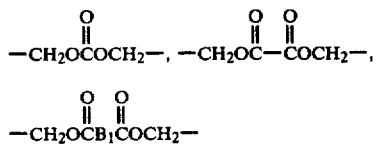

in which $B_1$ represents a divalent $C_1-C_8$ hydrocarbon residue, $-COB_2OC-$ in which $B_2$ represents a divalent $C_1-C_5$ hydrocarbon residue, or

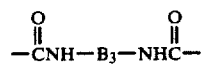

in which $B_3$ represents a divalent $C_1-C_3$ hydrocarbon residue;
and $R_8$ represents

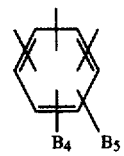

in which $B_4$ and $B_5$ each independently represents a $C_1-C_5$ hydrocarbon residue,

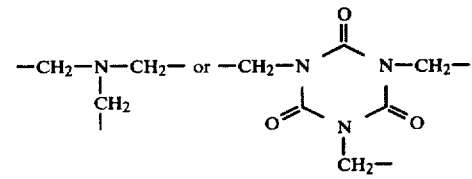

44. A cross-linked copolymer, which further comprises a structural unit of the formula(VI):

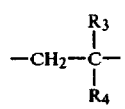
(VI)

wherein $R_3$ and $R_4$ each independently stand for a hydrogen atom, a halogen atom, a cyano group, an alkyl or alkenyl group having 1 to 5 carbon atoms, an aryl group, a halogenophenyl group, a phenyl group mono-, di- or tri-substituted with one or more substituents selected from $C_1-C_5$ straight chain or branched alkyl, haloalkyl, alkoxy and cyano groups, $-COOA_1$ in which $A_1$ represents a hydrogen atom or a $C_1-C_{10}$ hydrocarbon residue, $-COA_2$ in which $A_2$ represents a $C_1-C_{10}$ hydrocarbon residue, $-OCOA_3$ in which $A_3$ represents a $C_1-C_{10}$ hydrocarbon residue, $-CONHA_4$ in which $A_4$ represents a hydrogen atom or a $C_1-C_{10}$ hydrocarbon residue, an imidazolyl group, a pyridyl group or a carbazolyl group.

45. A process for the preparation of a cross-linked copolymer consisting of a structural unit of the formula(V), a structural unit of the formula(VI) and either or both of the structural units of the formula(VII) and (VIII):

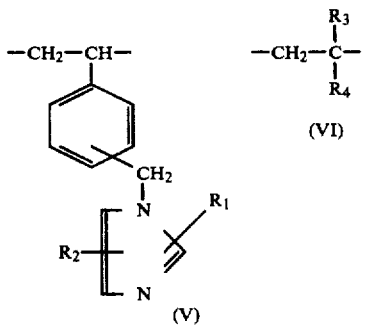

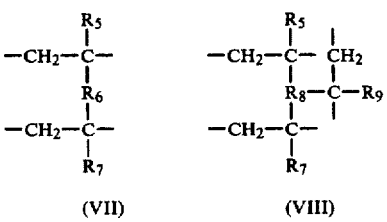

wherein
$R_1$ and $R_2$ each independently stand for a hydrogen atom, a straight chain or branched alkyl group having 1 to 17 carbon atoms, a phenyl group unsubstituted or substituted with one or more substituents selected from $C_1-C_8$ straight chain or branched alkyl groups, halogen atoms and an amino group, a naphthyl group, an aralkyl group having as an alkyl moiety a $C_1-C_4$ straight chain or branched alkylene group and as an aryl moiety a phenyl group unsubstituted or substituted with one or more substituents selected from halogen atoms and an amino group, a pyridyl group unsubstituted or substituted with one or more substituents selected from $C_1-C_4$ straight chain or branched alkyl groups, halogen atoms and an amino group, or a nitro group;

$R_3$ and $R_4$ each independently stand for a hydrogen atom, a halogen atom, a cyano group, an alkyl or alkenyl group having 1 to 5 carbon atoms, an aryl group, a halogenophenyl group, a phenyl group mono-, di- or tri-substituted with one or more substituents selected from $C_1-C_5$ straight chain or branched alkyl, haloalkyl, alkoxy and cyano groups, $-COOA_1$ in which $A_1$ represents a hydrogen atom or a $C_1-C_{10}$ hydrocarbon residue, $-COA_2$ in which $A_2$ represents a $C_1-C_{10}$ hydrocarbon residue, $-OCOA_3$ in which $A_3$ represents a $C_1-C_{10}$ hydrocarbon residue, $-CONHA_4$ in which $A_4$ represents a hydrogen atom or a $C_1-C_{10}$ hydrocarbon residue, an imidazolyl group, a pyridyl group or a carbazolyl group;

$R_5$, $R_7$ and $R_9$ each independently stand for a hydrogen atom or a methyl group;

$R_6$ stands for

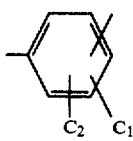

in which $C_1$ and $C_2$ each independently represent a $C_1$-$C_5$ hydrocarbon residue,

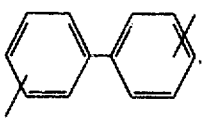

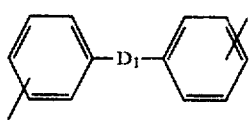

in which $D_1$ represents —O—, —S—, —NH— or a $C_1$-$C_5$ alkylane group, —SO—, —CO—,

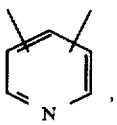

—CH₂—NH—CH₂—,

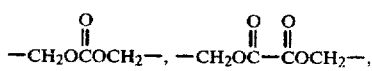

in which $B_1$ represents a divalent $C_1$-$C_8$ hydrocarbon residue,

in which $B_2$ represents a divalent $C_1$-$C_5$ hydrocarbon residue, or

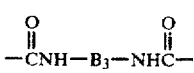

in which $B_3$ represents a divalent $C_1$-$C_3$ hydrocarbon residue;
and $R_8$ represents

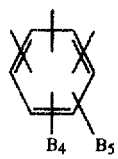

in which $B_4$ and $B_5$ each independently represent a $C_1$-$C_5$ hydrocarbon residue,

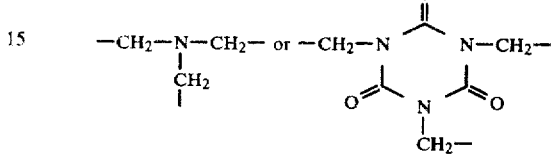

which comprises copolymerizing a basic compound of the formula(I):

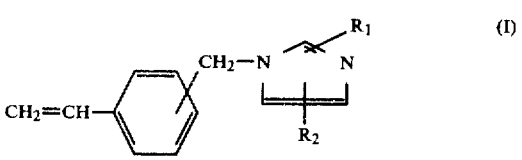

wherein $R_1$ and $R_2$ are as defined above, with a monomer of the formula (IX) and at least one monomer selected from the group consisting of a monomer of the formula(X) and a monomer of the formula(XI):

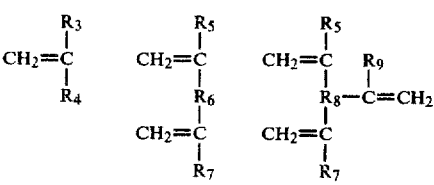

wherein $R_3$, $R_4$, $R_5$, $R_6$, $R_7$, $R_8$ and $R_9$ are as defined above.

46. A method of ion exchange which comprises contacting with an aqueous ferric chloride solution a crosslinked copolymer consisting of a structural unit of the formula(V), a structural unit of the formula(VI) and either or both of the structural units of the formula(VII) and (VII):

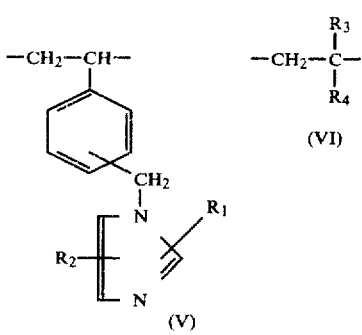

-continued

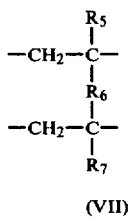 (VII)

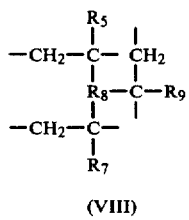 (VIII)

wherein

R₁ and R₂ each independently stand for a hydrogen atom, a straight chain or branched alkyl group having 1 to 17 carbon atoms, a phenyl group unsubstituted or substituted with one or more substituents selected from C₁-C₈ straight chain or branched alkyl groups, halogen atoms and an amino group, a naphthyl group, an aralkyl group having as an alkyl moiety a C₁-C₄ straight chain or branched alkylene group and as an aryl moiety a phenyl group unsubstituted or substituted with one or more substituents selected from halogen atoms and an amino group, a pyridyl group unsubstituted or substituted with one or more substituents selected from C₁-C₄ straight chain or branched alkyl groups, halogen atoms and an amino group, or a nitro group;

R₃ and R₄ each independently stand for a hydrogen atom, a halogen atom, a cyano group, an alkyl or alkenyl group having 1 to 5 carbon atoms, an aryl group, a halogenophenyl group, a phenyl group mono-, di- or tri-substituted with one or more substituents selected from C₁-C₅ straight chain or branched alkyl, haloalkyl, alkoxy and cyano groups, —COOA₁ in which A₁ represents a hydrogen atom or a C₁-C₁₀ hydrocarbon residue, —COA₂ in which A₂ represents a C₁-C₁₀ hydrocarbon residue, —OCOA₃ in which A₃ represents a C₁-C₁₀ hydrocarbon residue, —CONHA₄ in which A₄ represents a hydrogen atom or a C₁-C₁₀ hydrocarbon residue, an imidazolyl group, a pyridyl group or a carbazolyl group;

R₅, R₇ and R₉ each independently stand for a hydrogen atom or a methyl group;

R₆ stands for

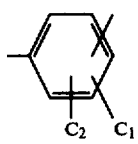

in which C₁ and C₂ each independently represent a C₁-C₅ hydrocarbon residue,

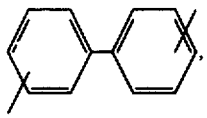

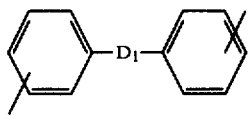

in which D₁ represents —O—, —S—, —NH— or a C₁-C₅ alkylene group, —SO—, —CO—,

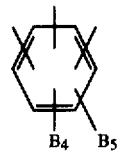

—CH₂—NH—CH₂—,

—CH₂OCOCH₂—, —CH₂OC(O)—C(O)OCH₂—,

—CH₂OCB₁COCH₂— in which B₁ represents a divalent C₁-C₈ hydrocarbon residue,

—COB₂OC— in which B₂ represents a divalent C₁-C₅ hydrocarbon residue, or

—CNH—B₃—NHC— in which B₃ represents a divalent C₁-C₃ hydrocarbon residue;
and R₈ represents

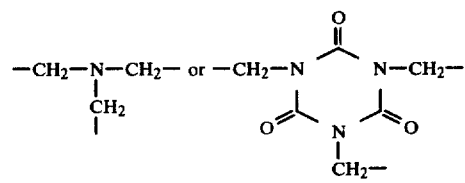

in which B₄ and B₅ each independently represent a C₁-C₅ hydrocarbon residue,

—CH₂—N—CH₂— or —CH₂—N(CO)N—CH₂—
         |                      |
         CH₂                    (ring with CH₂—)

* * * * *